(12) United States Patent
Breslin et al.

(10) Patent No.: US 10,111,841 B2
(45) Date of Patent: Oct. 30, 2018

(54) STABILIZATION OF ALCOHOL INTOXICATION-INDUCED CARDIOVASCULAR INSTABILITY

(71) Applicants: Jerome William Breslin, Tampa, FL (US); Travis Matthew Doggett, Tampa, FL (US)

(72) Inventors: Jerome William Breslin, Tampa, FL (US); Travis Matthew Doggett, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 15/185,802

(22) Filed: Jun. 17, 2016

(65) Prior Publication Data
US 2017/0020826 A1 Jan. 26, 2017

Related U.S. Application Data

(60) Provisional application No. 62/182,254, filed on Jun. 19, 2015.

(51) Int. Cl.
*A61K 31/137* (2006.01)
*A61K 31/661* (2006.01)
(Continued)

(52) U.S. Cl.
CPC .......... *A61K 31/137* (2013.01); *A61K 31/397* (2013.01); *A61K 31/426* (2013.01);
(Continued)

(58) Field of Classification Search
CPC ................ A61K 31/137; A61K 31/397; A61K 31/4245; A61K 31/426; A61K 31/51;
(Continued)

(56) References Cited

U.S. PATENT DOCUMENTS

| | | |
|---|---|---|
| 7,838,562 B2 | 11/2010 | Hla et al. |
| 2014/0100195 A1 | 4/2014 | Caldwell et al. |
| 2014/0309190 A1 | 10/2014 | Thomas et al. |

FOREIGN PATENT DOCUMENTS

| | | |
|---|---|---|
| WO | WO 02/051439 | 7/2002 |
| WO | WO 2005/054215 | 6/2005 |

(Continued)

OTHER PUBLICATIONS

Fryer et al. (2012) The Clinically-tested S1P Receptor Agonists, FTY720 and BAF312, Demonstrate Subtype-Specific Bradycardia (S1P1) and Hypertension (S1P3) in Rat. PLoS ONE 7(12): e52985 (Year: 2012).*
(Continued)

*Primary Examiner* — Angela C Brown-Pettigrew
(74) *Attorney, Agent, or Firm* — Saliwanchik, Lloyd & Eisenschenk

(57) ABSTRACT

The present invention concerns use of an agent that increases sphingosine-1-phosphate (S1P) receptor activity, such as S1P, or an S1P receptor agonist, for treatment of alcohol-intoxicated subjects will help stabilize blood pressure and improve resuscitation efforts in alcohol-intoxicated subjects, including alcohol-intoxicated trauma patients. Another aspect concerns a kit for stabilization of alcohol-intoxicated subjects, comprising an agent that increases S1P receptor activity.

6 Claims, 10 Drawing Sheets

(51) Int. Cl.
A61K 31/397 (2006.01)
A61K 31/4245 (2006.01)
A61K 31/426 (2006.01)
A61K 31/51 (2006.01)
A61K 31/515 (2006.01)
A61K 31/553 (2006.01)
A61K 31/662 (2006.01)

(52) U.S. Cl.
CPC .......... *A61K 31/4245* (2013.01); *A61K 31/51* (2013.01); *A61K 31/515* (2013.01); *A61K 31/553* (2013.01); *A61K 31/661* (2013.01); *A61K 31/662* (2013.01)

(58) Field of Classification Search
CPC .. A61K 31/515; A61K 31/553; A61K 31/662; A61K 31/661
See application file for complete search history.

(56) References Cited

FOREIGN PATENT DOCUMENTS

| | | |
|---|---|---|
| WO | WO 2005/123677 | 12/2005 |
| WO | WO 2006/010544 | 2/2006 |
| WO | WO 2006/100631 | 9/2006 |
| WO | WO 2006/100633 | 9/2006 |
| WO | WO 2006/100635 | 9/2006 |
| WO | WO 2006/137019 | 12/2006 |
| WO | WO 2007/060626 | 5/2007 |
| WO | WO 2007/080542 | 7/2007 |
| WO | WO 2007/086001 | 8/2007 |
| WO | WO 2008/029306 | 3/2008 |
| WO | WO 2008/029370 | 3/2008 |
| WO | WO 2008/029371 | 3/2008 |
| WO | WO 2008/035239 | 3/2008 |
| WO | WO 2008/114157 | 9/2008 |
| WO | WO 2009/024905 | 2/2009 |
| WO | WO 2009/025767 | 2/2009 |

OTHER PUBLICATIONS

Narkiewicz et al (Circulation. 2000;101:398-402) (Year: 2000).*
Adachi, K. et al. "FTY720 Story. Its Discovery and the Following Accelerated Development of Sphingosine 1-Phosphate Receptor Agonists as Immunomodulators Based on Reverse Pharmacology" *Perspectives in Medicinal Chemistry*, 2007, 1:11-23.
Adamson, R.H. et al. "Epac/Rap1 pathway regulates microvascular hyperpermeability induced by PAF in rat mesentery" *Am J Physiol Heart Circ Physiol*, Jan. 4, 2008, 294:H1188-H1196.
Adamson, R.H. et al. "Sphingosine-1-phosphate modulation of basal permeability and acute inflammatory responses in rat venular microvessels" *Cardiovascular Research*, 2010, 88:344-351.
Biello, J. et al. "Acute Ethanol Intoxication and the Trauma Patient: Hemodynamic Pitfalls" *World J Surg*, Jul. 12, 2011, 35:2149-2153.
Bird, M.D. et al. "Alcohol and trauma: a summary of the Satellite Symposium at the 30th Annual Meeting of the Shock Society" *Alcohol*, 2009, 43:247-252.
Bolli, M.H. et al. "2-Imino-thiazolidin-4-one Derivatives as Potent, Orally Active S1P$_1$ Receptor Agonists" *Journal of Medicinal Chemistry*, 2010, 53(10):4198-4211.
Bonitz, J.A. et al. "A Sphingosine-1 Phosphate Agonist (FTY720) Limits Trauma/Hemorrhagic Shock-Induced Multiple Organ Dysfunction Syndrome" *Shock*, 2009, 42(5):448-455.
Brinkmann, V. et al. "The Immune Modulator FTY720 Targets Sphingosine 1-Phosphate Receptors" *The Journal of Biological Chemistry*, Jun. 14, 2002, 277(24):21453-21457.
Brinkmann, V. et al. "Fingolimod (FTY720): discovery and development of an oral drug to treat multiple sclerosis" *Nature Reviews*, Nov. 2010, 9:883-897.
Camp, S.M. et al. "Synthetic Analogs of FTY720 [2-Amino-2-(2-[4-octylphenyl]ethyl)-1,3-propanediol] Differentially Regulate Pulmonary Vascular Permeability in Vivo and in Vitro" *The Journal of Pharmacology and Experimental Therapeutics*, 2009, 331(1):54-64.
Cherpitel, C.J. et al. "Alcohol-Related Injury in the ER: A Cross-National Meta-Analysis from the Emergency Room Collaborative Alcohol Analysis Project (ERCAAP)" *Journal on Studies on Alcohol*, Sep. 2003, 64:641-649.
Curry, F.E. et al. "Erythrocyte-derived sphingosine-1-phosphate stabilizes basal hydraulic conductivity and solute permeability in rat microvessels" *American Journal of Physiology Heart and Circulatory Physiology*, Oct. 1, 2012, 303(7):H825-H834.
Curry, F-.R. E. et al. "Tonic regulation of vascular permeability" *Acta Physiol*, Apr. 2013, 207(4):628-649.
Cusack, K.P. et al. "S1P1 receptor agonists: Assessment of selectivity and current clinical activity" *Curr. Op. in Dr. Disc. and Dev.*, Jul. 2010, 13(4):481-488, abstract.
Doggett, T.M. et al. "Acute Alcohol Intoxication-Induced Microvascular Leakage" *Alcohol Clin Exp Res*, Sep. 2014, 38(9):2414-2426.
Dudek, S.M. et al. "Pulmonary Endothelial Cell Barrier Enhancement by FTY720 Does Not Require the S1P$_1$ Receptor" *Cellular Signaling*, Aug. 2007, 19(8):1754-1764.
Fabbri, A. et al. "Blood Alcohol Concentration and Management of Road Trauma Patients in the Emergency Department" *The Journal of Trauma Injury, Infection, and Critical Care*, Mar. 2001, 50(3):521-528.
Fu, Y. et al. "Fingolimod for the Treatment of Intracerebral Hemorrhage: A 2-Arm Proof-of-Concept Study" *JAMA Neurology*, 2014, 71(9):1092-1101.
Greiffenstein, P. et al. "Alcohol Binge Before Trauma/Hemorrhage Impairs Integrity of Host Defense Mechanisms During Recovery" *Alcoholism Clinical and Experimental Research*, Apr. 2007, 31(4):704-715.
Hawksworth, J.S. et al, "Lymphocyte Modulation with FTY720 Improves Hemorrhagic Shock Survival in Swine" *PLoS ONE*, Apr. 30, 2012, 7(4):e34224(1-9).
Heckbert, S.A. et al. "Outcome after hemorrhagic shock in trauma patients" *J Trauma*, 1998, 45(3):545-549, abstract.
Hla, T. et al. "Sphingosine 1-phosphate (S1P): Physiology and the effects of S1P receptor modulation" *Neurology*, Feb. 22, 2011, 76(8 Suppl 3):S3-S8, abstract.
Howard, R.J. et al. "Alcohol-Binding Sites in Distinct Brain Proteins: The Quest for Atomic Level Resolution" *Alcohol Clin Exp Res*, Sep. 2011, 35(9):1561-1573.
Hsiao, S-.H. et al. "Effects of Exogenous Sphinganine, Sphingosine, and Sphingosine-1-Phosphate on Relaxation and Contraction of Porcine Thoracic Aortic and Pulmonary Arterial Rings" *Toxicological Sciences*, 2005, 86(1):194-199.
Jurkovich, G.J. et al. "Effects of Alcohol Intoxication on the Initial Assessment of Trauma Patients" *Annals of Emergency Medicine*, Jun. 1992, 21(6):704-708.
Kappos, L. et al. "Oral Fingolimod (FTY720) for Relapsing Multiple Sclerosis" *The New England Journal of Medicine*, Sep. 14, 2006, 355(11):1124-1140.
Kennedy, S. et al. "Targeting sphingosine-1-phosphate signalling for cardioprotection" *Current Opinion in Pharmacology*, 2009, 9:194-201.
Kimizuka, K. et al. "Sphingosine 1-Phosphate (S1P) Induces S1P2 Receptor-Dependent Tonic Contraction in Murine Iliac Lymph Vessels" *Microcirculation*, 2013, 20:1-16.
Lee, J-. F. et al. "Balance of S1P$_1$ and S1P$_2$ signaling regulates peripheral microvascular permeability in rat cremaster muscle vasculature" *American Journal of Physiology Heart and Circulatory Physiology*, Jan. 2009, 296(1):H33-H42.
Li, Q. et al. "Differential activation of receptors and signal pathways upon stimulation by different doses of sphingosine-1-phosphate in endothelial cells" *Exp Physiol*, 2015, 100(1):95-107.
Lu, L. et al. "Fingolimod exerts neuroprotective effects in a mouse model of intracerebral hemorrhage" *Brain Research*, Mar. 25, 2014, 1555:89-96.
Madan, A.K. et al. "Alcohol and drug use in victims of life-threatening trauma" *J Trauma*, 1999, 47(3):568-571, abstract.

(56) References Cited

OTHER PUBLICATIONS

Mathis, K.W. et al. "Altered Hemodynamic Counter-Regulation to Hemorrhage by Acute Moderate Alcohol Intoxication" *Shock*, 2006, 26(1):55-61.

Mathis, K.W. et al. "Transient central cholinergic activation enhances sympathetic nervous system activity but does not improve hemorrhage-induced hypotension in alcohol-intoxicated rodents" *Shock*, Oct. 2009, 32(4):410-415.

Molina, P.E. et al. "Consequences of alcohol-induced early dysregulation of responses to trauma/hemorrhage" *Alcohol*, 2004, 33:217-227.

Molina, M.F. et al. "Alcohol Does Not Modulate the Augmented Acetylcholine-Induced Vasodilatory Response in Hemorrhaged Rodents" *Shock*, 2009, 32(6):604-607.

Olivera, A. et al. "Sphingosine kinase 1 and sphingosine-1-phosphate receptor 2 are vital to recovery from anaphylactic shock in mice" *The Journal of Clinical Investigation*, May 2010, 120(5):1429-1440.

Phelan, H. et al. "Impact of Alcohol Intoxication on Hemodynamic, Metabolic, and Cytokine Responses to Hemorrhagic Shock" *The Journal of Trauma Injury, Infection, and Critical Care*, Apr. 2002, 52(4):675-682.

Pickering, T.G. et al. "Recommendations for Blood Pressure Measurement in Humans and Experimental Animals" *Circulation*, Feb. 8, 2005, 111:697-716.

Rolland, W.B. et al. "Fingolimod reduces cerebral lymphocyte infiltration in experimental models of rodent intracerebral hemorrhage" *Experimental Neurology*, Mar. 2013, 241:45-55.

Samarska, I.V. et al. "S1P$_1$ Receptor Modulation Preserves Vascular Function in Mesenteric and Coronary Arteries after CPB in the Rat Independent of Depletion of Lymphocytes" *PLoS ONE*, May 2014, 9(5):e97196(1-14).

Sammani, S. et al. "Differential Effects of Sphingosine 1-Phosphate Receptors on Airway and Vascular Barrier Function in the Murine Lung" *Am J Respir Cell Mol Biol*, 2010, 43:394-402.

Sanchez, T. et al. "Phosphorylation and Action of the Immunomodulator FTY720 Inhibits Vascular Endothelial Cell Growth Factor-induced Vascular Permeability" *The Journal of Biological Chemistry*, Nov. 21, 2003, 278(47):47281-47290.

Sanchez, T. et al. "Induction of Vascular Permeability by the Sphingosine-1-Phosphate Receptor-2 (S1P2R) and its Downstream Effectors ROCK and PTEN" *Arterioscler Thromb Vasc Biol*, Jun. 2007, 27:1312-1318, Data Supplement (1-8), Figures (1-5).

Shih, H.C. et al. "Alcohol Intoxication Increases Morbidity in Drivers Involved in Motor Vehicle Accidents" *American Journal of Emergency Medicine*, Mar. 2003, 21(2):91-94.

Stephenson, M. et al. "Deliberate Fingolimod Overdose Presenting with Delayed Hypotension and Bradycardia Responsive to Atropine" *Journal of Medical Toxicology*, 2014, 10:215-218.

Strader, C.R. et al. "Fingolimod (FTY720): A Recently Approved Multiple Sclerosis Drug Based on a Fungal Secondary Metabolite" *Journal of Natural Products*, Apr. 1, 2011, 74:900-907.

Sugiyama, A. et al. "Effects of Sphingosine 1-Phosphate, a Naturally Occurring Biologically Active Lysophospholipid, on the Rat Cardiovascular System" *Jpn. J. Pharmacol.*, 2000, 82:338-342.

Tharakan, B. et al. "α-Lipoic Acid Attenuates Hemorrhagic Shock-Induced Apoptotic Signaling and Vascular Hyperpermeability" *Shock*, 2008, 30(5):571-577.

Tharakan, B. et al. "Curcumin inhibits reactive oxygen species formation and vascular hyperpermeability following haemorrhagic shock" *Clinical and Experimental Pharmacology and Physiology*, 2010, 37:939-944.

Tharakan, B. et al. "Cyclosporine A Prevents Vascular Hyperpermeability After Hemorrhagic Shock by Inhibiting Apoptotic Signaling" *The Journal of Trauma Injury, Infection, and Critical Care*, 2009, 66(4):1033-1039.

Tharakan, B. et al. "(−)-Deprenyl inhibits Vascular Hyperpermeability Following Hemorrhagic Shock" *Shock*, Jan. 2010, 33(1):56-63.

Vonghia, L. et al. "Acute alcohol intoxication" *European Journal of Internal Medicine*, 2008, 19:561-567.

Wang, L. et al. "FTY720-Induced Human Pulmonary Endothelial Barrier Enhancement is Mediated by c-Abl" *The European Respiratory Journal*, Jul. 2011, 38(1):78-88.

Wang, L. et al. "FTY720 (s)-Phosphonate Preserves S1PR1 Expression and Exhibits Superior Barrier Protection to FTY720 in Acute Lung Injury" *Critical Care Medicine*, Mar. 2014, 42(3):1-21.

Whitaker, A.M. et al. "Augmented central nitric oxide production inhibits vasopressin release during hemorrhage in acute alcohol-intoxicated rodents" *American Journal of Physiology Regulatory, Integrative and Comparative Physiology*, Nov. 2011, 301(5):1-21.

\* cited by examiner

STABILIZATION OF ALCOHOL INTOXICATION-INDUCED CARDIOVASCULAR INSTABILITY

CROSS-REFERENCE TO RELATED APPLICATION

The present application claims the benefit of U.S. Provisional Application Serial No. 62/182,254, filed Jun. 19, 2015, which is hereby incorporated by reference herein in its entirety, including any figures, tables, nucleic acid sequences, amino acid sequences, or drawings.

GOVERNMENT SUPPORT

This invention was made with government support under Grant Number HL098215 awarded by the National Institutes of Health. The government has certain rights in the invention.

BACKGROUND OF THE INVENTION

Acute alcohol intoxication is a significant health problem in the United States and contributes to an increased risk of traumatic injury, accounting for the majority of alcohol-related disorders encountered in emergency rooms [17,41]. Frequent drinkers, reported as those individuals who drink on a weekly basis, are six times more likely to be admitted to the emergency room than individuals who drink infrequently [7]. Nearly 40% of injured patients admitted to the ER have intoxicating BAC greater than 80 mg/dL [7,22,38,41]. Intoxicated trauma patients often present with increased initial injury severity compared to non-intoxicated patients [18,38]. In addition, these patients typically require a significantly greater frequency of interventions in the hospital such as endotracheal intubations, placement of intracranial monitoring devices, and greater use of diagnostic peritoneal lavage [18].

One particularly problematic outcome that can occur with acute alcohol intoxication is aggravated hemodynamic instability following hemorrhage [33]. Intoxicated trauma patients are significantly more hypotensive upon arrival to the emergency department compared to non-intoxicated patients. Clinical studies have demonstrated that this low mean arterial blood pressure (MABP) in alcohol-intoxicated patients is a predictor of poor outcomes [3,16,41]. In addition, these patients require significantly greater volumes of intravenous crystalloid resuscitative fluids and blood products, despite the fact that there is no increase in severity of injury or difference in the international normalized ratio (used in determining the time blood takes to clot) compared to non-intoxicated patients [3,12,33]. Several studies have postulated that an impaired baroreceptor reflex or associated neural, endocrine, and metabolic mechanisms that control vascular tone may be responsible for this increased hypotension [14,24,26,27]. This is supported by the findings that: 1) significantly less blood from alcohol-intoxicated rats is required to produce the same hypotensive pressure during a fixed-pressure hemorrhage; and 2) with fixed-volume hemorrhage, alcohol-intoxicated rats are significantly more hypotensive following equal volumes of removed blood [24,27]. The elevations in plasma levels of epinephrine, norepinephrine, and arginine vasopressin to fixed-pressure hemorrhage are all significantly blunted in alcohol intoxicated rats compared to non-intoxicated animals [26]. However, more recent studies have shown that sympathetic control of blood pressure and acetylcholine-induced vasodilation are not impaired by alcohol intoxication [23,25]. Intracerebroventricular administration of choline, a precursor of the preganglionic neurotransmitter acetylcholine, is unable to improve hemodynamic and neuroendocrine counter-responses to hemorrhagic shock in alcohol-intoxicated rats [23]. Furthermore, studies using isolated aorta and mesenteric arteries of intoxicated and non-intoxicated rats show that this impaired hemodynamic counter-regulation to hemorrhage is not due to a decrease in responsiveness of blood vessels to vasoconstrictors like phenylephrine, or vasodilators like acetylcholine [25].

BRIEF SUMMARY OF THE INVENTION

Traumatic injuries often are associated with alcohol intoxication, which causes a complex, altered physiologic state. A hallmark feature is hypotension (low blood pressure) in the cardiovascular system, which can significantly worsen outcomes for trauma patients due to poor tissue perfusion. Improving alcohol-induced hypotension is a goal to improve outcomes for these patients. Several studies have investigated the impact of alcohol on the baroreceptor reflex, neuroendocrine control, and local control of arterial tone, which are altered but do not fully explain the alcohol-induced hypotension. In recent years, the inventors discovered that alcohol impacts the microcirculation and lymphatics, which also have a key role in maintaining central blood volume. It was observed that alcohol intoxication increases microvascular leakage of albumin in the rat mesentery, which can produce edema. Second, alcohol causes mesenteric lymphatics to dilate and reduces their pump activity, which would cause these vessels to act more like a second capacitance vessel system than as a delivery system to return plasma proteins and fluids to the central circulation. Moreover, the inventors have found that alcohol worsens tissue blood flow and significantly elevates microvascular leakage in the rat mesentery following a two-hit model of combined alcohol intoxication and hemorrhagic shock. The inventors have determined that administration of the bioactive lipid sphingosine-1-phosphate (S1P) can improve mean arterial blood pressure and blood flow within the gut following acute alcohol intoxication in rats. S1P also reduces alcohol-induced leakage of plasma proteins. Using endothelial cell monolayer models, empirical evidence was developed showing that the barrier enhancing effects of S1P can be mediated by canonical S1P receptors, but may also involve non-receptor mediated effects. S1P is also reported to improve tone of collecting lymphatic vessels. Without being limited by theory, it is proposed that administration of agents that increase S1P activity such as S1P, or other S1P receptor agonists, attenuate alcohol-induced microvascular hyperpermeability, helping to stabilize their blood pressure and improve resuscitation efforts in alcohol-intoxicated subjects. In some embodiments, the subjects are alcohol-intoxicated trauma patients. In some embodiments, the trauma patients are hemorrhage trauma patients. In some embodiments, the alcohol-intoxicated patients are not trauma patients (not currently suffering from an acute trauma).

Figures 2A, 2B, 2C, 2D:
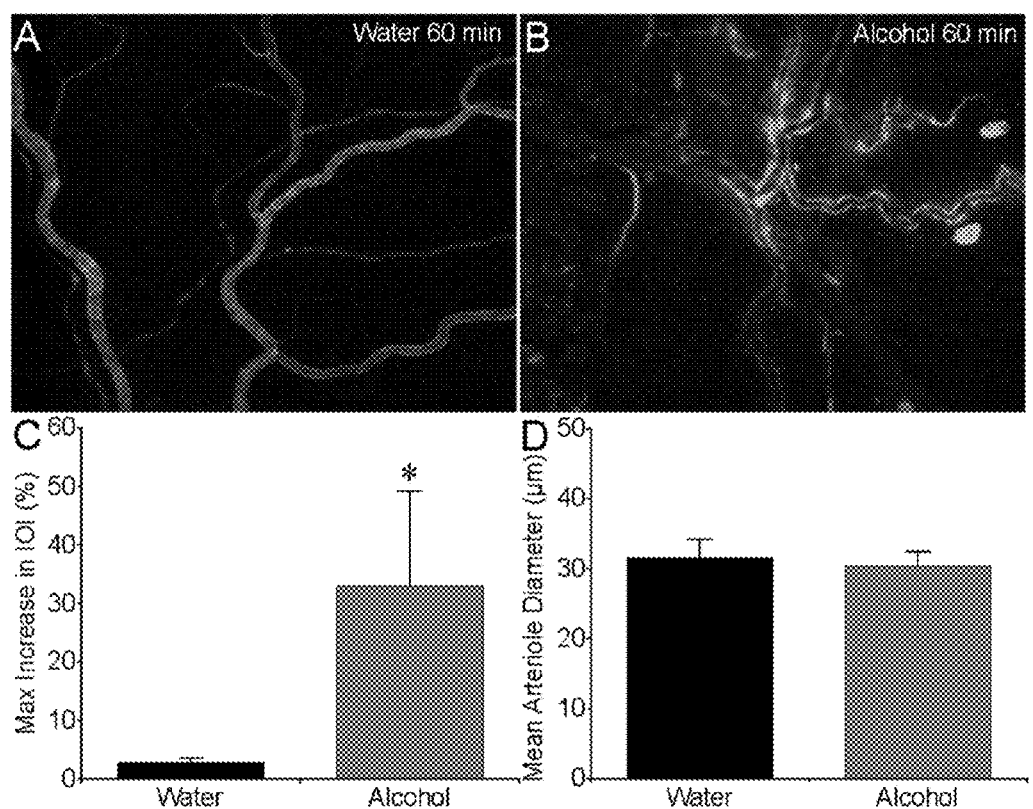

FIGS. 2A-2D. Acute alcohol intoxication stimulated microvascular hyperpermeability in the rat mesentery in vivo. FIG. 2A: Representative fluorescent image of the mesenteric microcirculation of a control rat that received water illustrating that FITC-albumin was present mainly inside the lumen of microvessels. FIG. 2B: Representative image of the mesenteric microcirculation from an alcohol-intoxicated rat in which many leaky sites where FITC-albumin has extravasated into the interstitial space are apparent. FIG. 2C: Mean maximum change in IOI in the extravascular space from the initial baseline just after FITC-albumin was injected i.v. to the end of the IVM experiment. FIG. 2D: Mean mesenteric arteriolar diameter in the observed microvascular beds. *P<0.05, alcohol vs. water. Mann-Whitney U-test, N=5 rats studied for the water group, and N=8 rats studied for the alcohol group [10].

Figures 3A, 3B, 3C, 3D:
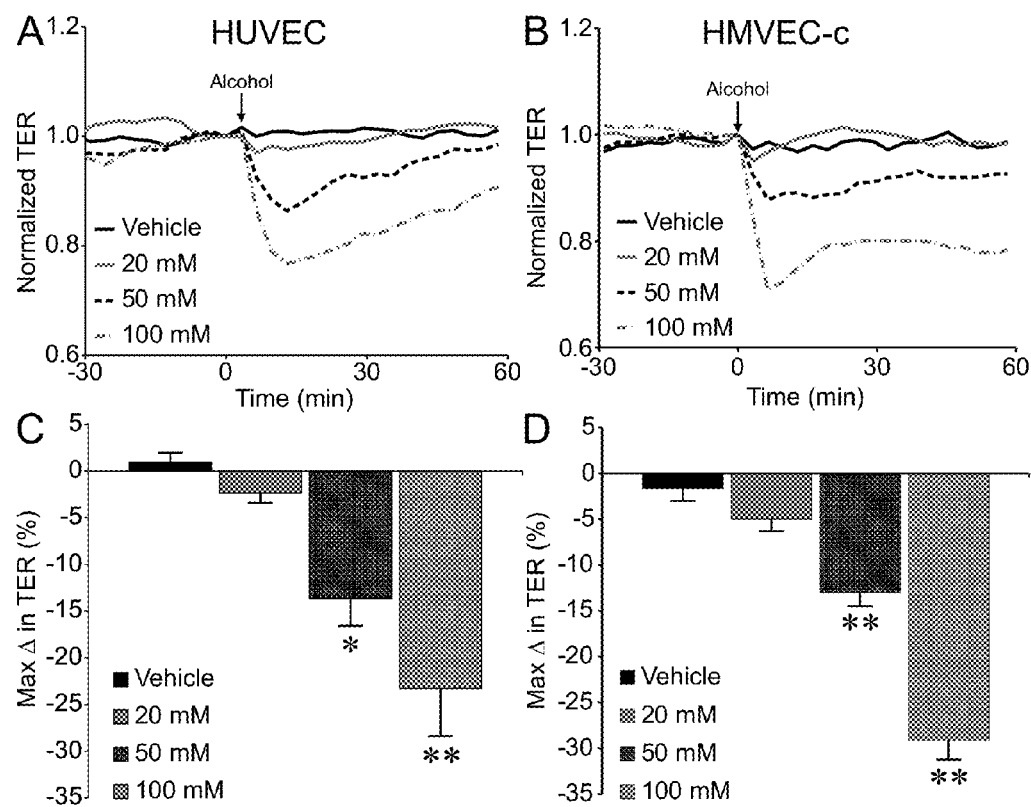

FIGS. 3A-3D. Alcohol-induced endothelial barrier dysfunction in cultured endothelial cell monolayers. FIG. 3A: Time-course of changes in transepithelial electrical resistance (TER) of HUVEC monolayers following application of vehicle (water) or 20, 50, or 100 mM alcohol. FIG. 3B: Time course of alcohol-induced changes in TER in HMVEC-C monolayers. FIG. 3C: The mean maximum alcohol-induced changes in TER in HUVEC. FIG. 3D: Mean maximum alcohol-induced changes in TER in HMVEC-c. *P<0.05 and **P<0.01 vs. vehicle. One-way ANOVA followed by Dunnett's test, all groups, N=4. [10]

Figures 4A, 4B:
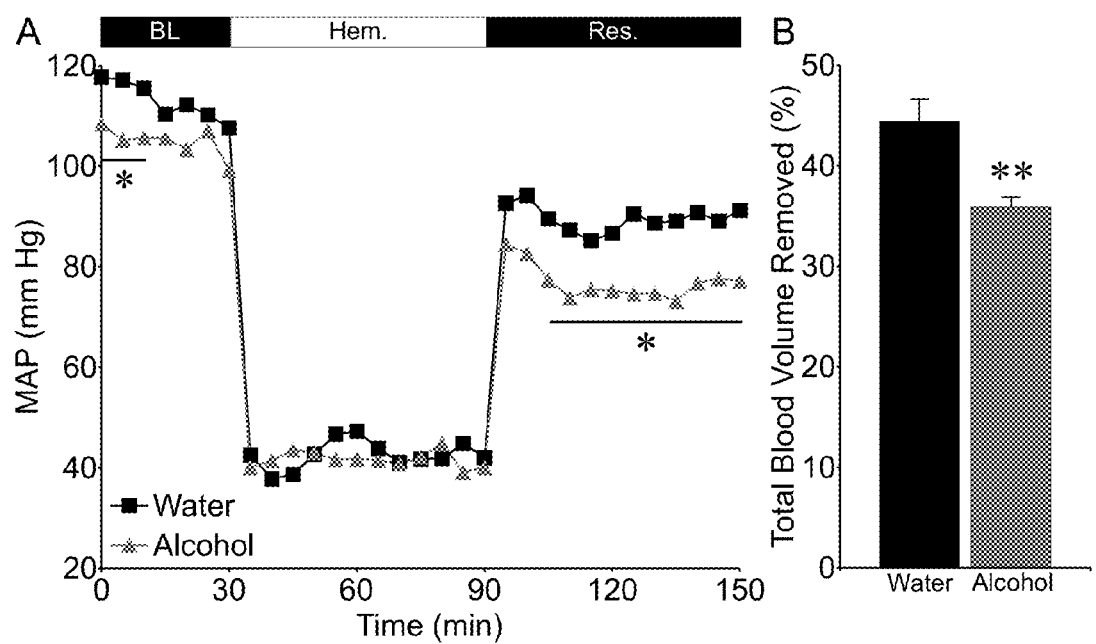

FIGS. 4A and 4B. Acute alcohol intoxication significantly decreased baseline MAP and blunted recovery of MAP during resuscitation following fix-pressure hemorrhage.

FIG. 4A: Time-course of changes in MAP of Sprague-Dawley rats treated with either 2.5 g/kg alcohol or isovolumic water during the HSR protocol. FIG. 4B: The % total blood volume removed (TBR) during the hemorrhage phase of the protocol for alcohol- and water-treated animals. *P<0.05 and **P<0.01 vs. water. Two-way ANOVA and unpaired T-test respectively, all groups, N=12.

Figures 5A, 5B, 5C, 5D, 5E:
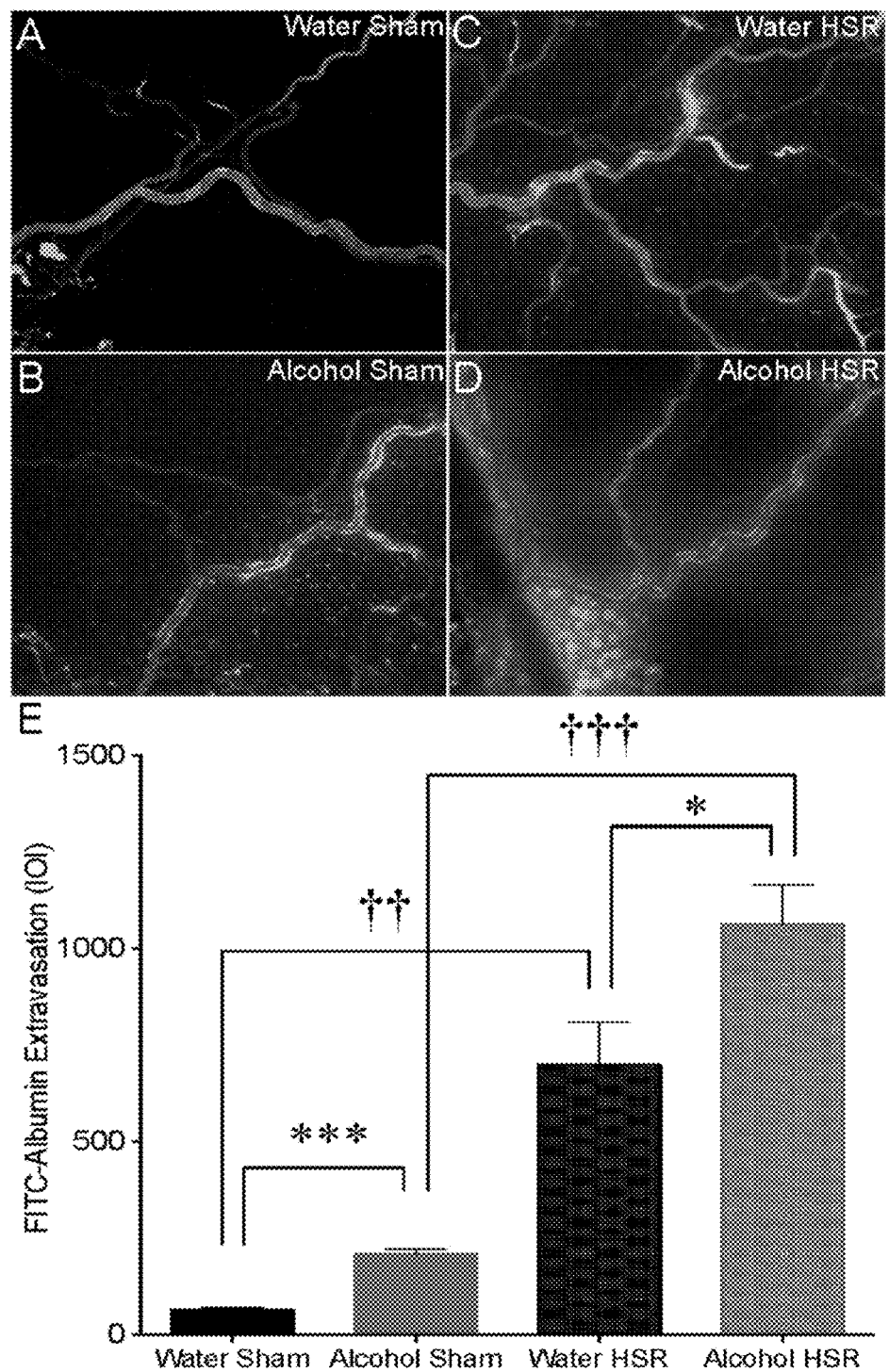

FIGS. 5A-5E. Acute alcohol intoxication combined with HSR significantly enhanced microvascular hyperpermeability in vivo. FIG. 5A: Representative fluorescent image of the mesenteric microcirculation of a rat that received water and undergoing sham-HSR illustrating that FITC-albumin was present mainly inside the lumen of microvessels. FIG. 5B: Representative image of the mesenteric microcirculation from an alcohol-sham rat in which many leaky sites where FITC-albumin has extravasated into the interstitial space are apparent. FIG. 5C: Representative image of the mesenteric microcirculation of a water-treated rat that underwent HSR. FIG. 5D: Representative image of the mesenteric microcirculation of an alcohol-treated rat that underwent HSR. FIG. 5E: Mean 60-minute RN in the extravascular space from the initial baseline just after FITC-albumin was injected i.v. to the end of the IVM experiment. ***p<0.001 vs. Water Sham; †† p<0.01 vs. Water Sham *p<0.05 vs. Water HS-R; ††† p<0.001 vs. Water HS-R. N=5 rats for the water-sham, N=7 for alcohol-sham, N=5 for water-HSR, N=6 for alcohol-HSR.

Figures 6A, 6B:
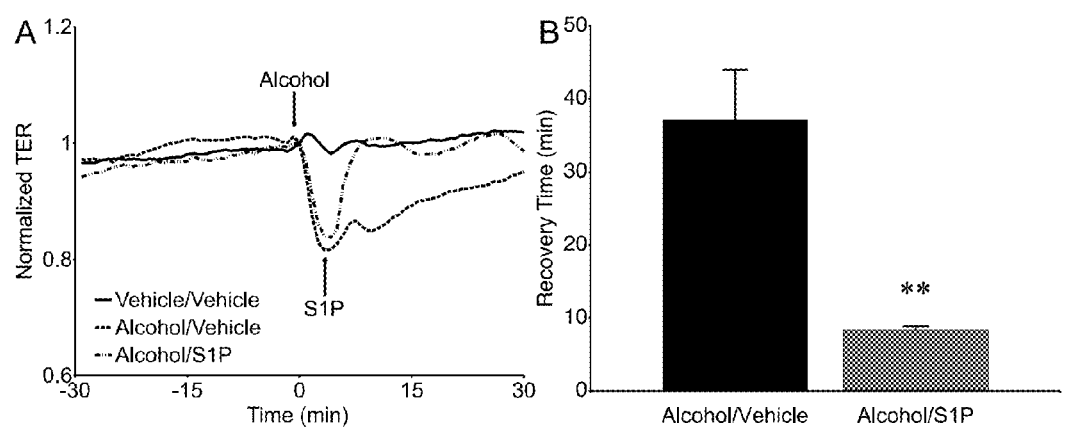

FIGS. 6A and 6B. Alcohol-induced barrier dysfunction in HUVEC was resolved faster by S1P treatment. HUVEC were cultured to confluence on gold-plated electrodes and then serum starved for 1-2 hours. Following 30 minutes of baseline TER measurements, alcohol was added to the wells to a final concentration of 50 mM for 5 minutes before treatment with 1 μM of S1 or vehicle. FIG. 6A: Time course of changes in HUVEC monolayer TER in response to 50 mM alcohol, followed by addition of 1 μM S1P 5 min later, or vehicle (PBS) 5 min later. FIG. 6B: Mean recovery time for HUVEC, i.e., time to return to baseline TER, starting from the time point immediately preceding alcohol was added. **P<0.01 versus alcohol/vehicle group. Statistical analysis by t-test; all HUVEC groups, N=8.

Figures 7A, 7B, 7C:
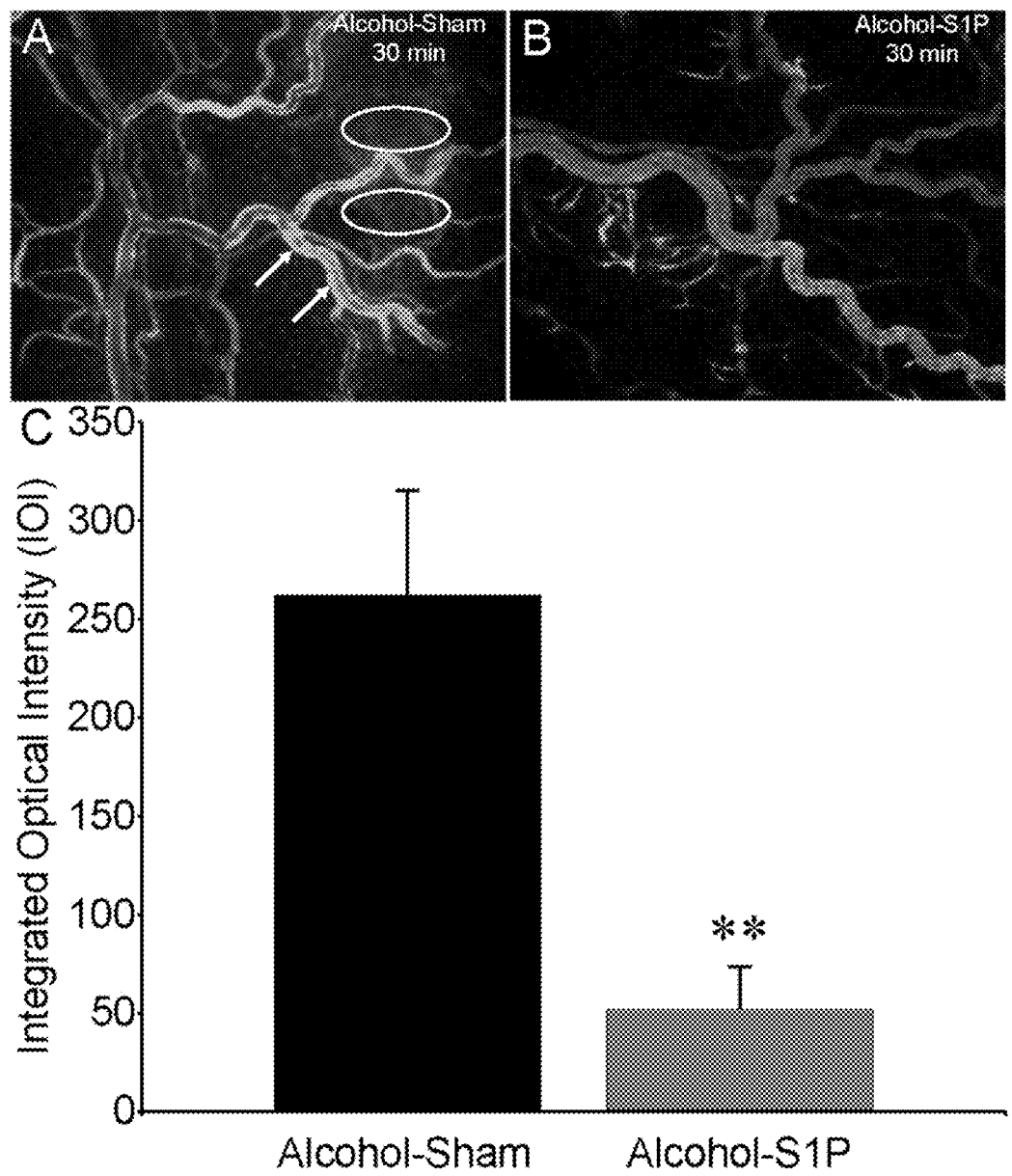

FIGS. 7A-7C. Infusion of S1P attenuated acute alcohol intoxication-stimulated microvascular hyperpermeability in vivo. FIG. 7A: Representative fluorescent image of the mesenteric microcirculation from an alcohol-intoxicated rat that received vehicle infusion, in which many leaky sites where FITC-albumin has extravasated into the interstitial space are apparent. White circles highlight areas of FITC-Albumin fluorescence in the surrounding interstitium. White arrows indicate areas of FITC-Albumin accumulation resulting in hotspots of fluorescence within and just outside the vessel walls. FIG. 7B: Representative fluorescent image of the mesenteric microcirculation of an alcohol-intoxicated rat that received S1P infusion, with FITC-albumin present mainly inside the lumens of microvessels. FIG. 7C: Mean maximum change in IOI in the extravascular space, from the initial baseline just after FITC-albumin was injected i.v. **P<0.01, Alcohol-Sham. Statistical analysis by t-test; both treatment groups, N=8.

Figure 8:
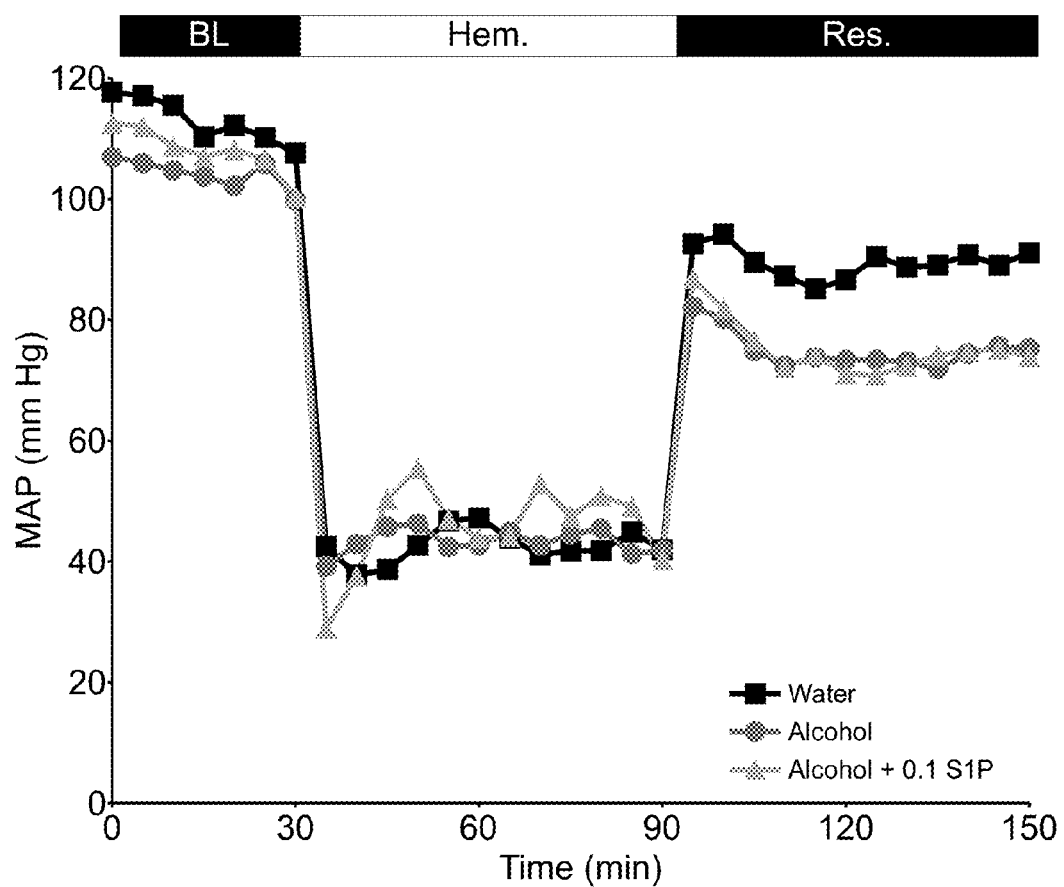

FIG. 8. Administration of S1P within resuscitation fluid does not prevent blunted recovery of MAP during resuscitation in alcohol-intoxicated animals. The time-course of changes in MAP of Sprague-Dawley rats treated with alcohol, water, or alcohol and 0.1 mg/kg S1P within the resuscitation fluid during the HSR protocol. Presence of S1P within the resuscitation fluid failed to recover MAP in alcohol-intoxicated rats to that of water-treated animals.

Figure 9:
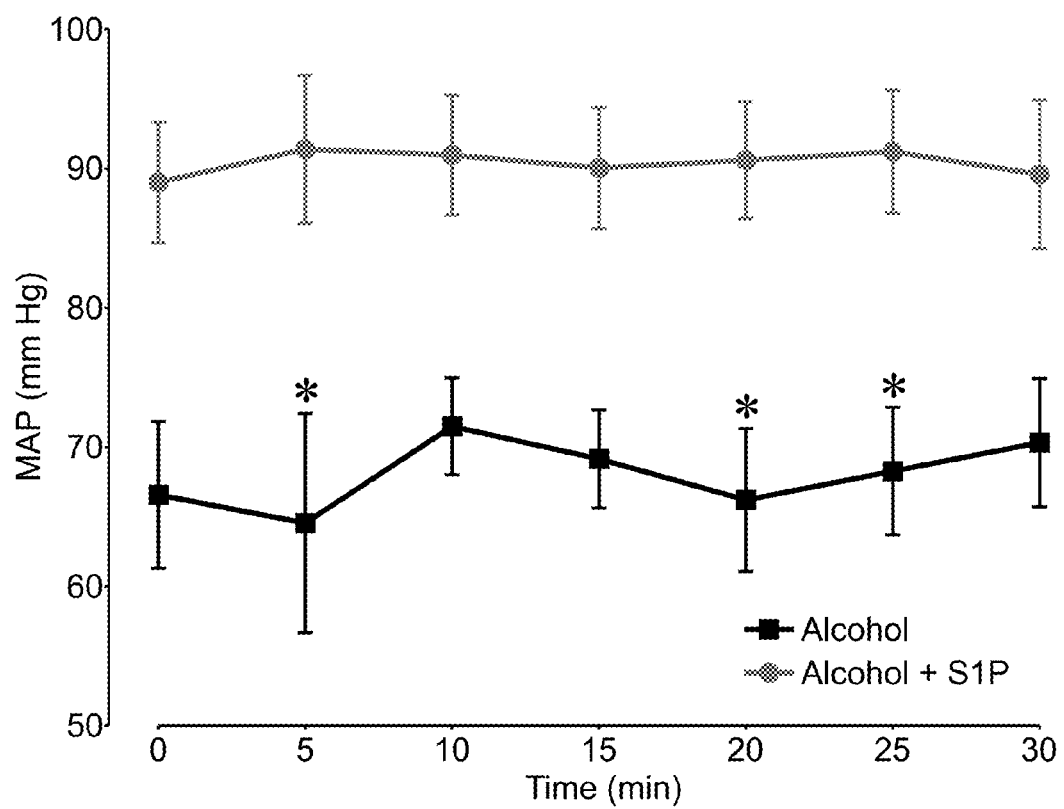

FIG. 9. S1P-infused Sprague-Dawley rats have improved MAP during IVM following HSR. The time-course of changes in MAP of Sprague-Dawley rats treated with alcohol, water, or alcohol and 0.1 mg/kg S1P within the resuscitation fluid during the IVM stage. Alcohol-intoxicated animals that received 0.1 mg/kg S1P in the resuscitation fluid demonstrated improved MAP compared with animals that received standard lactated Ringer's.

Figures 10A, 10B, 10C:
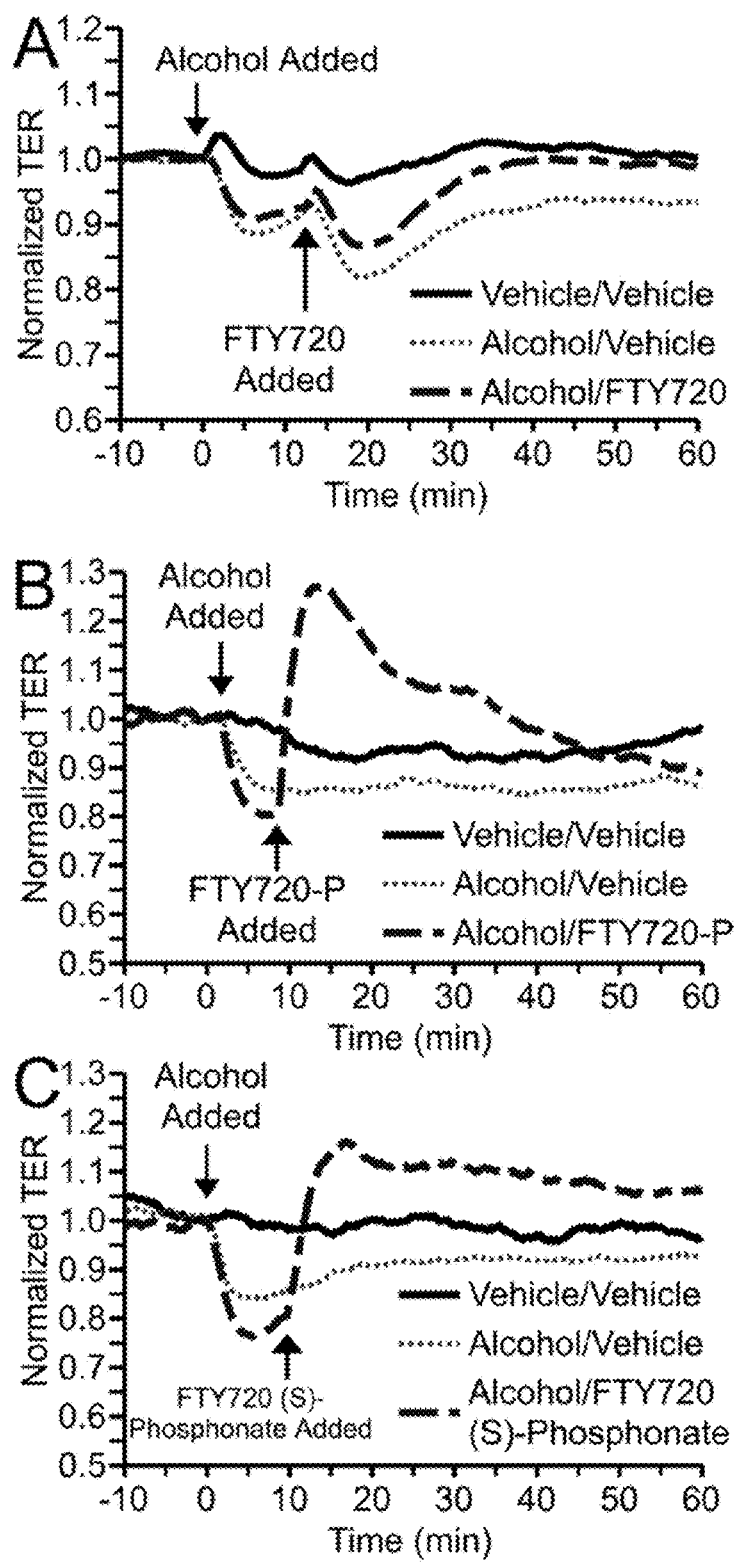

FIGS. 10A-10C. Selective S1P1R agonist FTY720-phosphonate ameliorates alcohol-induced microvascular hyperpermeability. FTY720 and its analogs reverse alcohol-induced disruption of EC monolayer barrier function. In all panels, 50 mM alcohol or vehicle was applied first, and 10 min later, 1 μM of FTY720 (FIG. 10A) FTY720-P (FIG. 10B) or FTY720 (S)-phosphonate (FIG. 10C) or vehicle was added. FIGS. 10A and 10C show data from HUVEC, while FIG. 10B shows data from cardiac microvascular EC. A minimum of N=4 monolayers in each group.

DETAILED DESCRIPTION OF THE INVENTION

Traumatic injury is the number one killer of healthy individuals. Alcohol intoxication is typically found in trauma patients. Alcohol-induced hypotension is a significant clinical problem, particularly when patients are in shock or have lost blood. Conventional fluid resuscitation typically is not very effective in alcohol-intoxicated patients.

The inventors investigated whether alcohol impacts vascular mechanisms other than those that focus on vascular tone. One such potential mechanism behind alcohol-induced hypotension following hemorrhage is a reduction in central fluid volume due to elevated microvascular permeability.

The inventors recently demonstrated that alcohol intoxication causes microvascular leakage in the mesentery [10]. The inventors have now investigated whether alcohol-induced microvascular hyperpermeability contributes to the hypotension.

Because hypotension is a strong predictor of poor outcomes, the inventors have developed a new strategy to ameliorate alcohol-induced hypotension based on their findings. The invention involves activation of sphingosine-1-phosphate (S1P) receptors, either by its endogenous agonist S1P, or by other exogenous receptor agonists. S1P receptors are ubiquitous throughout the body, and the effects of S1P throughout the body can collectively stabilize blood pressure. The agent that increases S1P receptor activity may stabilize blood pressure, for example, by causing a reduction (partially or fully resolving) alcohol-induced endothelial barrier dysfunction. Stabilization of blood pressure may be determined using methods known in the art such as by measurement of transepithelial electrical resistance (TER). For example, the agent may reduce the recovery time for TER to a reestablished normal or baseline for the subject.

Typically, the extent of intoxication is one resulting in alcohol-induced hypotension in the subject. Thus, the methods of the invention also include amelioration of alcohol-induced hypotension in the subject by administration of an effective amount of an agent that increases sphingosine-1-phosphate (S1P) receptor activity in the subject. In some embodiments, administration of the one or more agents causes improvement in endothelial barrier integrity (at least to a level that is a medically healthy level or normal for that subject). In some embodiments, administration of the one or more agents causes sustained improvement of endothelial barrier integrity (at least to a level that is a medically healthy level or normal for that subject) for a period of time, e.g., sixty minutes or longer.

Optionally, the subject may be identified as an alcohol-intoxicated subject prior to administration of the agent to the subject. In some embodiments, the methods of the invention include measuring the extent of alcohol intoxication in the subject (e.g., by measuring blood alcohol concentration (BAC), ethanol in saliva, or large osmolar gap (gap between measured and calculated plasma osmolality)), or otherwise determining whether the individual is suffering from alcohol intoxication (e.g., by observable symptoms of intoxication), before, during, and/or after administration of the agent. BAC measurement may be done directly by blood analysis or by breath testing, for example.

In some embodiments, the methods of the invention include measuring the subject's blood pressure before, during, and/or after administration of the agent to the subject. This may be useful in detecting or monitoring hypotension in the subject. Various methods for measuring blood pressure may be utilized, including a variety of techniques and devices, such as those described in Pickering TG et al., *Circulation*, 2005, 111:697-716, which is incorporated herein by reference in its entirety. Useful techniques include, for example, auscultatory, oscillometric, palpation, and use of obliteration of the pulse wave on a pulse oximeter. Mercury, aneroid, or hybrid sphygmomanometers may be used. Other techniques that may be used include the finger cuff method of Penaz, ultrasound, and tonometry. Manual or automated systems may be used.

Accordingly, in some embodiments, the methods of the invention include administering the agent to a subject in which blood pressure has been measured, extent of intoxication has been determined, or both.

In some embodiments, the method further comprises evaluating one or more times whether S1P receptor activity has increased in the subject after administration of the agent.

In some embodiments, the method further comprises evaluating one or more times following administration of the agent whether endothelial barrier enhancement actions on the microcirculation has occurred (to reduce endothelial hyper permeability and subsequent loss of central fluid volume to the extravascular space as occurred).

Agents that may be administered to a subject to increase S1P activity include, but are not limited to, S1P or an S1P agonist.

In some embodiments, S1P is delivered to the subject in its natural state. Optionally, the S1P can include one or more modifications at one or both ends of the molecule, and/or internally.

S1P Agonists

In some embodiments, the agent that increases S1P receptor activity is an agonist of one or more S1P receptors. Selective $S1P_1$ receptor agonists are compounds which preferentially activate the human $S1P_1$ receptor sub-type from among the $S1P_1$, $S1P_2$, $S1P_3$, $S1P_4$, and $S1P_5$ family members of sphingosine-1-phosphate-sensitive human G-protein coupled receptors. S1P receptor agonists decrease the number of circulating lymphocytes in peripheral blood in humans or animals after e.g., oral administration, therefore they have therapeutic potential in a variety of diseases associated with a dysregulated immune system. For example, the S1P receptor agonist FTY720 has been found to reduce the rate of clinical relapses in multiple sclerosis patients (Kappos L et al., *N Engl J Med.*, 2006 Sep. 14, 355(11): 1124-40).

S1P receptor agonists useful in the invention may be identified on the basis of their ability to produce endothelial barrier enhancement actions on the microcirculation to reduce endothelial hyperpermeability and subsequent loss of central fluid volume to the extravascular space. Typically, the agonists have greater affinity for the S1P receptor 1 (S1PR1), as this is the receptor responsible for the barrier enhancing effects of S1P. Permeability assays may be used in vitro to assess the effectiveness of these compounds on permeability in cultured cells and isolated vessels. These include transendothelial electrical resistance measurements and transwell assays. In some embodiments, the agonists have no affinity for S1PR2, or little affinity for S1PR2 relative to the affinity for S1PR1. The S1PR2 receptor does not become activated until S1P levels are much higher than the reported physiological concentration (0.5-4 μM) and activated RhoA pathways which are barrier disruptive. Treatments that act as a negative inotrope or negative chronotrope can be detrimental in trauma patients, particularly hemorrhage patients.

In some embodiments, the agent that increases S1P receptor activity is FTY720 or an FTY720 analog or derivative thereof. FTY720 is a compound structurally similar to S1P with demonstrated barrier-enhancing activity, similar to S1P. See Adachi et al., *Perspect Medicin Chem*, 2007, 1:11-23; and Camp et al. *J Pharmacol Exp Ther*, 2009, 331:54. FTY720, FTY, and Fingolimod are used interchangeably, referring to 2-amino-2-(4-octylphenethyl)propane-1,3-diol (Fingolimod). FTY720 is clinically approved for treating multiple sclerosis, in which it acts as an anti-inflammatory. The drug is a S1P receptor agonist selectively activating S1P receptor 1 (S1PR1). This receptor is selective for S1P and produces the desired endothelial barrier enhancement actions of S1P. In some embodiments, the S1P receptor agonist is phosphorylated or unphosphorylated FTY720. In some embodiments, the S1P receptor agonist comprises FTY720-phosphate (FTY720P). In some embodiments, the S1P receptor agonist comprises FTY720 (S)-phosphonate.

As used herein, the term "FTY720 derivative or analog" refers to a class of compounds, natural or synthetic, that are structurally similar to FTY720 suitable for use in the instant invention but the term does not encompass FTY720 (2-amino-2-(4-octylphenethyl)propane-1,3-diol; Fingolimod).

FTY720 derivatives or analogs include, without limitation, the (R) or (S) enantiomer of FTY720-phosphonate, the (R) or (S) enantiomer of FTY720-enephosphonate, and the (R) or (S) enantiomer of FTY720 regioisomer (3-(aminomethyl)-5-(4-octylphenyl)pentane-1,3-diol), or pharmaceutically acceptable salts thereof. In some embodiments, the FTY720 derivative or analog has one or more phosphate or phosphonate groups.

In some embodiments, the FTY720 analog or derivative is an FTY720-phosphonate, including the (R) and (S) enantiomers of FTY720-phosphonate, i.e., enantiomerically enriched or purified preparations of (R)- and (S)-3-amino-3-(hydroxymethyl)-5-(4-octylphenyl)pentylphosphonic acid, and the (R) and (S) enantiomer of FTY720-enephosphonate, i.e., enantiomerically enriched or purified preparations of (R)- and (S)-3-amino-3 -(hydroxymethyl)-5-(4-octylphenyl)pent-1-enylphosphonic acid. In some embodiments, the FTY720 analog or derivative is FTY720-phosphonate, including the (R) and (S) enantiomers of FTY720-phosphonate, i.e., enantiomerically enriched or purified preparations of (R)- or (S)-3-amino-3-(hydroxymethyl)-5-(4-octylphenyl)pentylphosphonic acid. In some embodiments, the FTY720 analog or derivative is (S)-FTY720-phosphonate. In some embodiments, the FTY720 analog or derivative does not include FTY720-phosphate (p-FTY720, FTY720P, or FTY720-P). Many S1P agonists are commercially available, such as CS 2100, CYM 50260, CYM 50308, CYM 5442 hydrochloride, CYM 5520, CYM 5541, RP 001 hydrochloride, SEW 2871, TC-G 1006, and TC-SP 14 (Tocris Bioscience).

SEW2871 (5-[4-phenyl-5-(trifluoromethyl)-2-thienyl]-3-[3-(trifluoromethyl)phenyl]-1,2,4-oxadiazole), CAS # 256414-75-2, is also obtainable from Cayman Chemical (Ann Arbor, Mich.)). SEW2871 is a selective S1P receptor agonist that is an immunosuppressant.

Selective $S1P_1$ receptor agonists also include those disclosed in the published PCT applications WO 2005/054215, WO 2005/123677, WO 2006/010544, WO 2006/100635, WO 2006/100633, WO 2006/100631, WO 2006/137019, WO 2007/060626, WO 2007/086001, WO 2007/080542, WO 2008/029371, WO 2008/029370, WO 2008/029306, WO 2008/035239, WO 2008/114157, WO 2009/024905, and WO 2009/025767, and are incorporated herein by reference in their entirety.

In some embodiments, an $S1P_1$ agonist based on the 2-imino-thiazolidin-4-one scaffold is used, such as the $S1P_1$ agonist in Bolli MH et al., *J Med Chem*, 2010, 53(10):4198-4211, which are incorporated herein by reference.

U.S. Pat. No. 7,838,562 (Hla T et al.) describes agonists of vascular endothelial SP1 receptors, and are incorporated herein by reference in their entirety.

U.S. Patent application publication 20140100195 (Caldwell RD et al.) describes compounds that have agonist activity at one or more S1P receptors, and are incorporated herein by reference in their entirety.

U.S. Patent application publication 20140309190 (Jermaine T et al.) describes bicyclic aryl compounds that have agonist activity at one or more of the S1P receptors.

In a further aspect, the invention provides therapeutic methods that use an S1P-receptor agonist, which refers to any molecule that induces S1P receptor biological activity, including downstream pathways mediated by S1P signaling; such as receptor binding and elicitation of a cellular response to S1P.

The S1P receptor agonists may be in the form of a pharmaceutically acceptable salt. The term "salt" refers to a pharmaceutically acceptable and relatively non-toxic, inorganic or organic acid addition salt of a compound of the present invention. Pharmaceutical salt formation consists in pairing an acidic, basic or zwitterionic drug molecule with a counterion to create a salt version of the drug. A wide variety of chemical species can be used in a neutralization reaction. Pharmaceutically acceptable salts of the invention thus include those obtained by reacting the main compound, functioning as a base, with an inorganic or organic acid to form a salt, for example, salts of acetic acid, nitric acid, tartric acid, hydrochloric acid, sulfuric acid, phosphoric acid, methane sulfonic acid, camphor sulfonic acid, oxalic acid, maleic acid, succinic acid or citric acid. Pharmaceutically acceptable salts of the invention also include those in which the main compound functions as an acid and is reacted with an appropriate base to form, e.g., sodium, potassium, calcium, magnesium, ammonium, or choline salts. Though most of salts of a given active principle are bioequivalents, some may have, among others, increased solubility or bioavailability properties. Salt selection is now a common standard operation in the process of drug development as taught by H. Stahl and C. G Wermuth in their handbook (Stahl H & Wermuth C G (2011) Pharmaceutical salts: Properties, selection, and use, 2nd ed. (Wiley-VCH, ed.).

In a preferred embodiment, the designation of a compound is intended to designate the compound per se, as well as any pharmaceutically acceptable salt, hydrate, isomer, or racemate thereof The term "agonist" implies no specific mechanism of biological action, and is deemed to expressly include and encompass all possible pharmacological, physiological, and biochemical interactions with the S1P receptor and its consequences which can be achieved by a variety of different, and chemically divergent, compositions. In one aspect, the S1P receptor agonists are sphingosine and S1P structural analogs which bind to an S1P receptor under physiological conditions in vitro or in vivo, wherein the binding exerts an agonistic effect on the S1P receptor. Agonists of all types of S1P receptors, such as S1P(1-5) are acceptable, but those of S1P1 are preferred. S1P structural analogs are believed to bind to the S1P binding site of S1P receptors. However, agonists may bind at sites other than the S1P binding site, provided such binding results in an agonistic effect. Typically, the agonists have greater affinity for the S1P receptor 1 (S1PR1), as this is the receptor responsible for the barrier enhancing effects of S1P. Permeability assays may be used in vitro to assess the effectiveness of these compounds on permeability in cultured cells and isolated vessels. These include transendothelial electrical resistance measurements and transwell assays. In some embodiments, the agonists have no affinity for S1PR2, or little affinity for S1PR2 relative to the affinity for S1PR1.

Examples of agonists include, but are not limited to, Fingolimod (also named FTY720, trade name GILENYA™, Novartis Pharma AG, New York), BAF312 (Novartis Pharma. AG, New York), Ponesimod (ACT-128800, Actelion Ltd., Switzerland), ONO-4641 (Ono Pharma, Japan), CS-0777 (Daiichi Sankyo, Japan), KRP-203 (Kyorin, Japan), PF-991 (Pfizer, New York), and W146 (Cayman Chemical, Michigan) (Brinkmann et al. (2010) Nat. Rev. 9: November 2010: 883-897; Hla T. et al. (2011) *Neurology* 2011; 76; S3; Cusack et al. (2010) *Curr. Op. in Dr. Disc. and Dev.* 13 (4): 481-488; Strader et al. (2011) J. Nat. Prod. 2011, 74, 900-907).

In aspects where the S1P receptor agonist is a small molecule, a small molecule can have a molecular weight of about any of 100 to 20,000 daltons, 500 to 15,000 daltons, or 1000 to 10,000 daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. Usually, when the S1P receptor agonist according to the invention is a small molecule, it will be administered at the rate of 0.1 to 300 mg/kg of the weight of the patient divided into one to three or more doses. For an adult patient of normal weight, doses ranging from 1 mg to 5 g per dose can be administered.

Kits Comprising Blood Pressure Stabilizing Agents of the Invention

The invention also provides kits comprising agents of the invention, which may be used, for example, for stabilizing alcohol-intoxicated patients. The kits may be used for any of the methods described herein, including, for example, to treat a subject with alcohol-induced intoxication. The kits may optionally provide additional components such as, buffers and instructions for use of an agent in any of the methods described herein. In some aspects, the kits include instructions for treating pain. In some aspects, the kit comprises an agent described herein and instructions for stabilizing blood pressure in an alcohol-intoxicated subject.

The kits of the invention are useful for storing and dispensing the agents that increase S1P activity described herein. In addition to such S1P activity increasing agents, the kit may further include one or more other components, including but not limited to, agents useful for treating or stabilizing alcohol intoxicated individuals. In some embodiments, the agent that increases S1P activity is S1P or an agonist of the S1P receptor. The kit comprises an agent that increases S1P activity in a subject; and one or more agents selected from the group consisting of: glucose, thiamine (vitamin B1), intravenous access device, intravenous fluid comprising normal saline (e.g., sodium chloride), benzodiazepine (e.g., such as lorazepam (Ativan), diazepam (Valium), or chlordiazepoxide (Librium)), or pentobarbital. The kits comprise one or more doses of the S1P receptor activity-increasing agent, and one or more additional components. In one embodiment, the kit comprises two of the foregoing additional components. In another embodiment, the kit comprises three of the foregoing additional components. In another embodiment, the kit comprises four of the foregoing additional components. In other embodiments, the agent is in solid (e.g., powder), liquid, or semi-solid form. The kit may include printed instructions for carrying out one or more steps of the methods described herein.

It should be appreciated that the kits of the invention are not limited to any particular container configuration. The container(s) can be constructed and arranged, and the agent can be prepared (e.g., solid or liquid), stored, and dispensed, in any of numerous ways within the scope of the invention. For example, in some embodiments, the kit includes a tray or other housing with one or more cavities of desirable geometries for receiving one or more components of the kit.

Containers for holding components of the kit can be rigid (such as canisters) or soft (such as bags or pouches), as needed or desired. Materials for constructing containers for medicaments in various physical states are known in the art. In some embodiments, the container(s) and housing is plastic, such as polypropylene. The kit is preferably packaged for ease of handling and use by the subject to be treated or by medical personnel. The kit is preferably sealed and sterilized.

The kit may contain one or more containers containing an S1P receptor activity-increasing agent and, optionally, other agents, contained in the same container or provided separately in individual containers. Each container may contain one or more doses of the S1P receptor activity-increasing agent.

As used herein, the term "S1P" refers to Sphingosine-1-Phosphate. An "S1P receptor", also referred to as "S1PR", refers to a polypeptide that is bound by or activated by S1P. S1P receptors include those of any mammalian species, including, but not limited to, human, canine, feline, equine, primate, or bovine. This definition includes S1P receptor subtypes S1P, S1P2, S1P3, S1P4 and S1P5, also known as $S1PR_1$, $S1PR_2$, $S1PR_3$, $S1PR_4$, and $S1PR_5$, respectively.

"Biological activity" of S1P generally refers to the ability to bind S1P receptors and activate S1P receptor signaling pathways, including but not limited to S1P1 receptor signaling pathways. Biologically active fragments and variants of S1P (i.e., those with biological activity) may be administered to the subject. Without limitation, a biological activity includes any one or more of the following: the ability to bind an S1P receptor, the ability to promote S1P receptor dimerization and phosphorylation; the ability to activate an S1P receptor signaling pathway; and the ability to produce endothelial barrier enhancement actions on the microcirculation to reduce endothelial hyperpermeability and subsequent loss of central fluid volume to the extravascular space. Typically, biologically active fragments and variants have greater affinity for the S1P receptor 1 (S1PR1), as this is the receptor responsible for the barrier enhancing effects of S1P. Permeability assays may be used in vitro to assess the effectiveness of fragments and variants on permeability in cultured cells and isolated vessels. These include transendothelial electrical resistance measurements and transwell assays.

As used herein, "substantiality pure" refers to material which is at least 50% pure (i.e., free from contaminants), more preferably at least 90% pure, more preferably at least 95% pure, more preferably at least 98% pure, more preferably at least 99% pure.

The subject is a mammal, such as a human. In some embodiments, the subject is an alcohol-intoxicated trauma patient. For example, the subject may have endured acute trauma. For example, the subject may be undergoing treatment in an emergency room (ER) setting. In some embodiments, the subject is a hemorrhage trauma patient. In other embodiments, the subject is not one suffering acute trauma at the time of administration. In some embodiments, the subject is not suffering from chronic alcoholism.

In some embodiments, the method further comprises identifying the subject as being alcohol-intoxicated and/or suffering from alcohol-intoxicated trauma prior to administering the agent that increases S1P receptor activity in the subject. In some embodiments, the subject is identified as an alcohol-intoxicated hemorrhage trauma patient prior to administration of the agent. Subjects may be identified as alcohol-intoxicated, or having alcohol-intoxicated trauma, and/or having hemorrhage by a qualified medical care provider (e.g., physician or nurse) by evaluating signs and/or symptoms known in the art.

As used herein, a "pharmaceutical composition" refers to a preparation of one or more of the active ingredients described herein (e.g., an agent that increases S1P receptor activity) with other components such as physiologically suitable carriers and excipients. The purpose of a pharmaceutical composition is to facilitate administration of an agent to the subject.

As used herein, the term "active ingredient" refers to the agent accountable for the intended biological effect (e.g., increase in S1P receptor activity). In some embodiments, the agent is S1P or a biologically active fragment or variant thereof In some embodiments, the agent is an agonist of the S1P receptor. As used herein, the phrases "physiologically acceptable carrier" and "pharmaceutically acceptable carrier," which may be used interchangeably, refer to a carrier or a diluent that does not cause significant irritation to the subject and does not abrogate the biological activity and properties of the administered agent.

As used herein, the term "excipient" refers to an inert substance added to a pharmaceutical composition to further facilitate administration of an active ingredient. Examples of excipients include, but are not limited to, calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration for agents that increase S1P receptor activity (e.g., S1P and S1P agonists) and the pharmaceutical compositions containing them may, for example, include oral, rectal, transmucosal, especially transnasal, intestinal, or parenteral delivery, including intramuscular, subcutaneous, and intramedullary injections, as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a subject.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated may be used in the formulation. Such penetrants are generally known in the art.

For oral administration, the pharmaceutical composition can be formulated readily by combining the active ingredient(s) with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added. Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, an "effective amount" means an amount of active ingredients (e.g., agent that increases S1P receptor activity) effective to prevent, delay onset of, alleviate, or ameliorate symptoms of a disorder (e.g., alcohol-induced microvascular hyperpermeability).

Determination of an effective amount is well within the capability of those skilled in the art in light of the detailed disclosure provided herein.

For any preparation used in the methods of the invention, the dosage or the effective amount can be estimated initially from in vitro and cell culture assays (e.g., permeability assays sucha s transendothelial electrical resistance measurements and transwell assays, and as further described herein below). For example, a dose can be formulated in animal models to achieve a desired concentration or titer. Such information can be used to more accurately determine useful doses in humans.

Exemplified Embodiments Of The Invention

Embodiment 1. A method for stabilizing blood pressure in an alcohol-intoxicated subject, comprising administering an effective amount of an agent that increases sphingosine-1-phosphate (S1P) receptor activity in the subject.

Embodiment 2. The method of embodiment 1, wherein the agent is S1P, or an agonist of the S1P receptor.

Embodiment 3. The method of embodiment 1 or 2, wherein the subject is suffering from acute physical trauma.

Embodiment 4. The method of embodiment 1 or 2, wherein the subject is not suffering from acute physical trauma. Embodiment 5. The method of any preceding embodiment, further comprising identifying the subject as being alcohol-intoxicated at the time of said administering.

Embodiment 6. The method of any preceding embodiment, further comprising measuring the extent of alcohol-intoxication in the subject before, during, and/or after said administering.

Embodiment 7. The method of any preceding embodiment, further comprising measuring the subject's blood pressure before, during, and/or after said administering.

Embodiment 8. The method of embodiment 1, wherein the agent comprises phosphorylated or unphosphorylated 2-amino-2-[2-(4-octaphenyl)ethyl]propane-1,3 diol (FTY720; Fingolimod).

Embodiment 9. The method of embodiment 1, wherein the agent comprises FTY720-phosphate (FTY720P) or FTY720 (S)-phosphonate.

Embodiment 10. The method of any preceding embodiment, wherein an S1P receptor agonist is administered to the subject, and wherein the agonist is selected from the group consisting of:
2-amino-2-[2-(4-octaphenyl)ethyl]propane-1,3 diol,
2-amino-2-methyl-4-[4-heptoxy-phenyl]butane-1-ol,
2-amino-3-phosphate-2-[2-4-octaphenyl)ethyl]propane-1-ol;
2-amino-2-methyl-4-[4-heptoxy-phenyl]1-diphosphoric acid;
or a combination of two or more of the foregoing agonists.

Embodiment 11. The method of embodiment 2, wherein the S1P receptor agonist is a selective agonist for the S1P1 receptor.

Embodiment 12. The method of embodiment 1 or 2, wherein the S1P receptor agonist is selected from the group consisting of Fingolimod, BAF312, ACT-128800, ONO-4641, CS-0777, KRP-203, PF-991, W146, and SEW2871, or a combination of two or more of the foregoing agonists.

Embodiment 13. The method of embodiment 1, wherein the agent is an agonist of the S1P receptor and has one or more phosphate or phosphonate groups.

Embodiment 14. The method of any preceding embodiment, wherein the subject has alcohol-induced hypotension, and wherein said administering ameliorates the alcohol-induced hypotension.

Embodiment 15. A kit comprising an agent that increases sphingosine-1-phosphate (S1P) receptor activity in a subject; and one or more agents selected from the group consisting of:
glucose,
thiamine (vitamin B1),
intravenous access device,
intravenous fluid comprising normal saline (e.g., sodium chloride),
benzodiazepine (e.g., such as lorazepam (Ativan), diazepam (Valium), or chlordiazepoxide (Librium)), or pentobarbital. Embodiment 16. The kit of embodiment 15, wherein the agent is S1P or an agonist of the S1P receptor.

Embodiment 17. The kit of embodiment 15, wherein the agent comprises phosphorylated or unphosphorylated 2-amino-2-[2-(4-octaphenyl)ethyl]propane-1,3 diol (FTY720; Fingolimod).

Embodiment 18. The kit of embodiment 15, wherein the agent comprises FTY720-phosphate (FTY720P) or FTY720 (S)-phosphonate.

Embodiment 19. The kit of embodiment 15, wherein agent is selected from the group consisting of:
2-amino-2-[2-(4-octaphenyl)ethyl]propane-1,3 diol,
2-amino-2-methyl-4-[4-heptoxy-phenyl]butane-1-ol,
2-amino-3-phosphate-2-[2-4-octaphenyl)ethyl]propane-1-ol;
2-amino-2-methyl-4-[4-heptoxy-phenyl]1-diphosphoric acid;
or a combination of two or more of the foregoing agonists.

Embodiment 19. The kit of embodiment 15, wherein the agent is a selective agonist for the S1P1 receptor.

Embodiment 20. The kit of embodiment 15, wherein agent is selected from the group consisting of Fingolimod, BAF312, ACT-128800, ONO-4641, CS-0777, KRP-203, PF-991, W146, and SEW2871, or a combination of two or more of the foregoing agonists.

Embodiment 21. The kit of embodiment 15, wherein the agent is an agonist of the S1P receptor, and has one or more phosphate or phosphonate groups.

All patents, patent applications, provisional applications, and publications referred to or cited herein, supra or infra, are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Acute Alcohol Intoxication Stimulated Microvascular Hyperpermeability In Vivo

Figure 1:
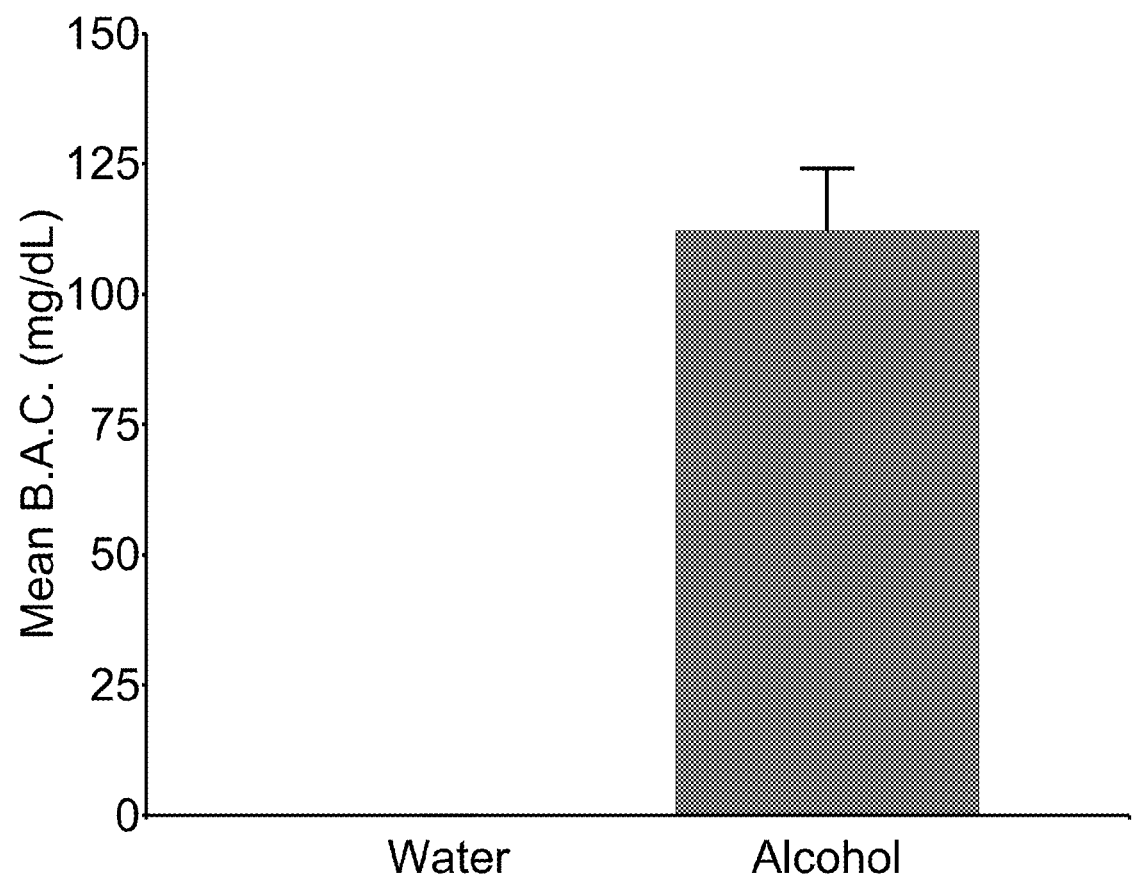
FIG. 1. Blood alcohol concentrations (BAC) 30 minutes after administration of 2.5-g/kg alcohol or isovolumic water. Intragastric catheters were implanted 2-3 days before the day of experiments. Male Sprague-Dawley rats were administered 2.5 g/kg alcohol or isovolumic water and allowed to freely roam in their cages for 30 minutes. Following 30 minutes incubation, experimental protocols were begun and blood samples obtained. Values are mean ±standard error of the mean. ***P<0.001 vs. Water, t-test, N=19-20 for each group.

Administration of a 2.5-g/kg dose of alcohol was performed via an intragastric catheter that was implanted 2-3 days before the day of experiment. The animals were allowed to roam freely for 30 minutes after administration. This dosage of alcohol produced intoxicating BAC within 30 minutes and was significantly higher than those animals in the time-matched, water-treated groups (FIG. 1). Sixty minutes after the start of IVM, alcohol-treated animals had noticeable extravasation of FITC-albumin from the mesenteric microcirculation compared to controls (FIGS. 2A and 2B). There is marked fluorescence in the surrounding interstitium in the alcohol rats as opposed to the water rats where the fluorescence remains within the vessels of the arterioles, capillaries, and venules. In addition, there is accumulation of FITC-Albumin within and just outside the vessel walls resulting in intense areas of fluorescence, or hotspots of FITC-Albumin extravasation. This extravasation was quantified by calculating the maximum change in IOI from baseline. The mean maximal change in IOI in the extravascular space adjacent to postcapillary venules was significantly higher in the alcohol-treated rats compared to control rats (FIG. 2C). Mean arteriolar diameter of third-order arterioles was also assessed to determine whether changes in blood flow may contribute to the overall permeability response. There was no significant difference in mean arteriolar diameter between the alcohol and control groups, supporting the notion that increased permeability of the venular endothelium primarily contributed to the observed macromolecule leakage (FIG. 2D).

These experiments demonstrate that acute alcohol intoxication in naive Sprague-Dawley rats can induce microvascular hyperpermeability to FITC-albumin in the mesenteric microcirculation compared to water-treated controls. In addition, the increase in hyperpermeability is not due to increases in the diameter of the arterioles, suggesting that increased filtration forces from an increase in capillary hydrostatic pressure is not responsible for the increased permeability of the microvessels.

EXAMPLE 2

Acute Alcohol Intoxication Significantly Decreased the Barrier Function of Cultured Endothelial Cells The direct impact of alcohol on endothelial barrier function was tested using cultured HUVEC or HMVEC-c confluent monolayers grown on gold-plated electrodes. Thirty minutes of baseline transepithelial electrical resistance (TER) measurements were recorded before the cells were treated with alcohol at final bath concentrations of 20, 50 or 100 mM. Alcohol was added directly into the MEDIA within the wells. For both HUVEC (FIG. 3A) and HMVEC-c (FIG. 3B), all concentrations of alcohol tested caused an immediate decline in the TER of the monolayer. The decrease in TER was alcohol concentration-dependent with high alcohol concentrations eliciting a larger drop in TER. The maximal decline in TER from baseline was significant for the 50 and 100 mM concentrations in both HUVEC (FIG. 3C) and HMVEC-c (FIG. 3D). These experiments demonstrated that acute alcohol intoxication alone had a direct effect on the endothelial monolayer and caused barrier compromise.

EXAMPLE 3

Acute Alcohol Intoxication Significantly Decreased Baseline MAP and Blunted Recovery of MAP During Resuscitation Following Fix-Pressure Hemorrhage The impact of alcohol intoxication combined with traumatic injury on microvascular hyperpermeability was assessed. A fixed-pressure hemorrhage and resuscitation (HSR) model previously described by Molina and colleagues was employed to achieve injury [23-27,41]. Animals had catheters implanted in the carotid artery, jugular vein, and an indwelling gastric catheter 3-4 days before the experiment. The animals were administered a 2.5-g/kg dose of alcohol or isovolumic and allowed to roam freely for 30 minutes. After 30 minutes, baseline MAP measurements were recorded for 30 minutes before the start of hemorrhage. Blood was shed to achieve a fixed-pressure of 40-60 mm Hg for 60 minutes and followed by resuscitation with lactated Ringer's solution for 60 minutes. MAP was monitored and recorded in real-time for the duration of the HSR protocol (FIG. 4A). Alcohol intoxicated animals presented with significantly lower baseline MAP compared with water-treated animals. In addition, recovery of MAP during the resuscitation phase was significantly blunted in alcohol-treated animals compared to water. The alcohol-exacerbated hypotension during hemorrhage is further illustrated by examining total blood volume removed (TBR) (FIG. 4B). Alcohol animals required significantly less of their total blood volume to be shed to achieve the 40-60 mm Hg target MAP compared to water-treated animals.

These results confirm the data seen by Molina and colleagues as well as the clinic in that alcohol intoxication induces hemodynamic instability and increased hypotension [4,23-27,33,41]. Alcohol intoxication induces hypotension in Sprague-Dawley rats during baseline and blunts recovery of MAP during hemorrhage. Further, the volume of blood removed during hemorrhage is significantly reduced with alcohol intoxication.

EXAMPLE 4

Acute Alcohol Intoxication Combined with HSR Significantly Enhanced Microvascular Hyperpermeability In Vivo Immediately following completion of the HSR protocol the animal was anesthetized and prepped for IVM. Sixty minutes after the start of IVM, alcohol-sham animals had noticeable extravasation of FITC-albumin from the mesenteric microcirculation compared to water shams (FIGS. 5A and 5B). As seen before with animals receiving only alcohol or water, there is marked fluorescence in the surrounding interstitium in the alcohol rats as opposed to the water rats where the fluorescence remains within the vessels of the arterioles, capillaries, and venules. In addition, there is accumulation of FITC-Albumin within and just outside the vessel walls resulting in intense areas of fluorescence, or hotspots of FITC-Albumin extravasation. Those animals treated with water combined with HSR also display fluorescence in the extravascular regions of the surrounding interstitium and hotspots of accumulation in the vessel walls consistent with results seen by fellow investigators [34-37] (FIG. 5C). Finally, animals that were administered alcohol even greater fluorescence in the surrounding interstitium that extravasates even further from the vasculature than seen in the alcohol-shams and water-HSR groups (FIG. 5D). This extravasation was quantified by calculating the mean 60-minute RM. The mean 60-minute IOI in the extravascular space adjacent to postcapillary venules was significantly higher in the alcohol-sham rats compared to water-sham rats while RN was significantly higher in alcohol-HSR rats compared to water-HSR rats (FIG. 5E).

These results demonstrate that alcohol has an exacerbating effect on HSR-induced microvascular hyperpermeability. This supports the inventors' hypothesis that the hemodynamic instability and hypotension seen in intoxicated patients following hemorrhage is due to loss of central fluid volume due to alcohol-induced microvascular hyperpermeability.

EXAMPLE 5

S1P significantly reduced recovery time of TER following alcohol treatment

The inventors next set out to determine if S1P could similarly reduce the recovery time for TER to be reestablished to baseline in HUVEC pretreated with alcohol. Following 30 minutes of baseline TER measurements, alcohol was added to the wells to a final concentration of 50 mM for 5 minutes before treatment with 1 µM S1P or vehicle. Treatment with S1P following alcohol caused the TER to rapidly rise to the previously established baseline levels, while a slow recovery occurred in vehicle groups (FIG. 6A). The recovery time was significantly reduced in the S1P-treated groups post-alcohol, reestablishing baseline TER about 30 minutes faster than cells treated with vehicle (FIG. 6B).

These data demonstrate that exogenous S1P could resolve alcohol-induced endothelial barrier dysfunction significantly faster similar to 8-CPT.

EXAMPLE 6

Infusion of S1P Significantly Attenuated Alcohol-Induced Microvascular Hyperpermeability In Vivo S1P has been used to reduce the permeability of rat microvessels to BSA, however, only one study has been performed in intact animals [1,2,8,9,30]. Using the inventors' established method of observing hyperpermeability in the rat mesentery, the ability of S1P to abolish or attenuate the enhanced extravasation of FITC-albumin caused by acute alcohol intoxication was examined. After receiving a 2.5 g/kg bolus of alcohol and allowed free roaming for 30 minutes, rats were prepared for IVM and administered S1P to a final concentration of 2 µM within the FITC-albumin infusion. This provided an estimated final plasma concentration of S1P in the rats of 0.2 µM. Rats that did not receive S1P in the FITC-albumin infusion displayed extravasation of FITC-albumin from the microcirculation into the surrounding tissues (white circles) as well as accumulation of FITC-Albumin within and just outside of the vessel walls (white arrows) resulting in intense areas of fluorescence, or hotspots of FITC-Albumin (FIG. 7A). On the other hand, rats that received 0.2 µM S1P in the infusion had a marked reduction in the extravasation of FITC-albumin (FIG. 7B). The mean IOI of the rats receiving S1P in the FITC-albumin infusion was significantly lower than those rats receiving FITC-albumin infusion alone (FIG. 7C).

These data demonstrate that exogenous STP infusion at physiological concentrations is capable of attenuating the microvascular hyperpermeability caused by acute alcohol intoxication significantly. This is evidenced by reduced extravasation of FITC-albumin into the surrounding interstitium of alcohol-intoxicated rats treated with STP compared to vehicle treated rats.

EXAMPLE 7

Administration of S1P within Resuscitation Fluid Does not Prevent Blunted Recovery of Map During Resuscitation in Alcohol-Intoxicated Animals The impact of STP infusion within the resuscitation fluid on the recovery of MAP following hemorrhage was assessed in alcohol-intoxicated rats. The HSR model previously described was employed with the addition of STP within the lactated Ringer's resuscitation fluid to a final dose of 0.1 mg/kg. The animals were administered a 2.5-g/kg dose of alcohol or isovolumic and allowed to roam freely for 30 minutes. After 30 minutes, baseline MAP measurements were recorded for 30 minutes before the start of hemorrhage. Blood was shed to achieve a fixed-pressure of 40-60 mm Hg for 60 minutes and followed by resuscitation containing S1P for 60 minutes. MAP was monitored and recorded in real-time for the duration of the HSR protocol (FIG. 8). Alcohol intoxicated animals receiving 0.1 mg/kg S1P within the resuscitation fluid presented with the same impaired recovery of MAP as animals that did not receive STP during resuscitation previously shown (FIGS. 4A and 4B). These results suggest that S1P is unable to restore MAP in alcohol-intoxicated animals compared to water-treated animals in the immediate phase of resuscitation.

EXAMPLE 8

S1P-Infused Sprague-Dawley Rats have Improved MAP During IVM Following HSR

As before, immediately following completion of the HSR protocol the animal was anesthetized and prepped for IVM. During IVM, MAP is continually monitored. Animals receiving 0.1 mg/kg S1P demonstrated improved MAP during this later stage of the protocol (FIG. 9). Alcohol-intoxicated animals receiving S1P during resuscitation had MAP between 20-25 mm Hg higher than the alcohol-intoxicated animals that received standard fluids. This improved MAP was significant at the 5, 20, and 25 minute time points for 30 minutes IVM performed. At the time of writing this, only 3 IVM experiments were performed with alcohol-intoxicated animals that received S1P during resuscitation.

These results demonstrate that while infusion of S1P within the resuscitation fluid does not help with the recovery of MAP in alcohol-intoxicated rats during the resuscitation phase, MAP is improved during the later stage of IVM compared to animals that received standard fluids. These results and those demonstrating S1P infusion attenuating alcohol-induced microvascular permeability suggests that S1P within the resuscitation fluid is restoring MAP by reducing microvascular hyperpermeability and subsequent loss of central fluid volume.

EXAMPLE 9

Selective S1P1R Agonist FTY720-Phosphonate Ameliorates Alcohol-Induced Microvascular Hyperpermeability S1P acts on at least five receptors to elicit diverse cellular responses in multiple tissues. Current evidence suggests that activation of S1P1R promotes endothelial barrier integrity, while S1P2R activation disrupts barrier integrity [20,32]. The S1P mimetic FTY720 (fingolimod) has the advantage that it activates all S1P receptors except S1P2R. FTY720 is phosphorylated by sphingosine kinase, to form FTY720-phosphate (FTY720-P), which in turn activates the S1P receptors [6,31]. FTY720 enhances endothelial barrier function in vitro [11,39] and reduces VEGF- and histamine-induced microvascular hyperpermeability in vivo [19,31]. FTY720 is currently FDA-approved for treatment of multiple sclerosis, and has been tested in the clinic to determine effectiveness for reducing inflammation after intracerebral hemorrhage [13,21,28]. A key finding supporting this aim is that FTY720 reduced hypotension and lung injury caused by combined hemorrhage and trauma (laparotomy) in anesthetized rats [5]. In a swine model of uncontrolled hemorrhage, FTY720 also improved survival, which was attributed to sequestration of lymphocytes into the mesenteric lymph nodes and spleen and reducing neutrophil-driven inflammation [15]. FTY720 has also been named a functional antagonist because it can cause proteasome-mediated turnover of S1P1R, which may account for some of its pleotropic effects. A novel analog, FTY720 (S)-phosphonate, limits this S1P1R turnover and produces longer-lasting endothelial barrier enhancement [40]. One potential concern is a report that 0.5 mg/kg FTY720 reduced baseline blood pressure in rats [29]. However, this study examined blood pressure several hours after FTY720 was administered. The rats were also anesthetized in that study, which typically facilitates decreases in MAP. Their observation may also be due to turnover of S1P1R over time. The novel compound FTY720 (S)-phosphonate can prevent this problem [40].

The data in FIG. 8 show that FTY720 and its analogs expedite the restoration of barrier integrity of cultured EC monolayers exposed to alcohol. FIGS. 10A-C show TER data. TER is an index of the barrier function of endothelial cells. After alcohol initially decreased barrier function, FTY720 accelerated its restoration to the baseline level observed in time-matched control EC monolayers, compared to alcohol alone (FIG. 10A). Unlike S1P, which restored the barrier in about 5 min (see FIG. 6A), FTY720 restored barrier function occurred gradually (FIG. 10A). This was probably due to the fact that FTY720 must be phosphorylated by sphingosine kinase before it can exert its activity, as application of phosphorylated FTY720 (FTY720-P) to the monolayers (FIG. 10B) resulted in a much more rapid elevation in barrier function. FTY720-P caused an overshoot over the original baseline, followed by a gradual drop over time. In comparison, the novel analog FTY720 (S)-phosphonate, applied after alcohol (FIG. 10C), also caused a rapid rescue of barrier function, rising above baseline levels. However, FTY720 (S)-phosphonate also caused a sustained enhancement of barrier integrity over time. Collectively, these data show the feasibility of using S1P1R agonists to rescue endothelial barrier function in the presence of alcohol, including the sustained improvement in endothelial barrier integrity with FTY720 (S)-phosphonate.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Adamson R H, Ly J C, Sarai R K, Lenz J F, Altangerel A, Drenckhahn D, and Curry F E. Epac/Rap1 pathway regulates microvascular hyperpermeability induced by PAF in rat mesentery. Am J Physiol Heart Circ Physiol 294: H1188-1196, 2008.

2. Adamson R H, Sarai R K, Altangerel A, Thirkill T L, Clark J F, and Curry F R. Sphingosine-1-phosphate modulation of basal permeability and acute inflammatory responses in rat venular microvessels. Cardiovasc Res 88: 344-351, 2010.

3. Bilello J, McCray V, Davis J, Jackson L, and Danos L A. Acute ethanol intoxication and the trauma patient: hemodynamic pitfalls. World J Surg 35: 2149-2153, 2011.

4. Bird M D, Choudhry M A, Molina P E, and Kovacs E J. Alcohol and trauma: a summary of the Satellite Symposium at the 30th Annual Meeting of the Shock Society. Alcohol 43: 247-252, 2009.

5. Bonitz J A, Son J Y, Chandler B, Tomaio J N, Qin Y, Prescott L M, Feketeova E, and Deitch E A. A sphingosine-1 phosphate agonist (FTY720) limits trauma/hemorrhagic shock-induced multiple organ dysfunction syndrome. Shock 42: 448-455, 2014.

6. Brinkmann V, Davis M D, Heise C E, Albert R, Cottens S, Hof R, Bruns C, Prieschl E, Baumruker T, Hiestand P, Foster C A, Zollinger M, and Lynch K R. The immune modulator FTY720 targets sphingosine 1-phosphate receptors. J Biol Chem 277: 21453-21457, 2002.

7. Cherpitel C J, Bond J, Ye Y, Borges G, MacDonald S, Stockwell T, Giesbrecht N, and Cremonte M. Alcohol-related injury in the ER: a cross-national meta-analysis from the Emergency Room Collaborative Alcohol Analysis Project (ERCAAP). Journal of studies on alcohol 64: 641-649, 2003.

8. Curry F E, Clark J F, and Adamson R H. Erythrocyte-derived sphingosine-1-phosphate stabilizes basal hydraulic conductivity and solute permeability in rat microvessels. Am J Physiol Heart Circ Physiol 303: H825-834, 2012.

9. Curry F R and Adamson R H. Tonic regulation of vascular permeability. Acta Physiol (Oxf) 207: 628-649, 2013.

10. Doggett T M and Breslin J W. Acute alcohol intoxication-induced microvascular leakage. Alcohol Clin Exp Res 38: 2414-2426, 2014.

11. Dudek S, Camp S, Chiang E, Singleton P, Usatyuk P, Zhao Y, Natarajan V, and Garcia J. Pulmonary endothelial cell barrier enhancement by FTY720 does not require the S1P1 receptor. Cellular signalling 19: 1754-1764, 2007.

12. Fabbri A, Marchesini G, Morselli-Labate A M, Rossi F, Cicognani A, Dente M, Iervese T, Ruggeri S, Mengozzi U, and Vandelli A. Blood alcohol concentration and management of road trauma patients in the emergency department. J Trauma 50: 521-528, 2001.

13. Fu Y, Hao J, Zhang N, Ren L, Sun N, Li Y J, Yan Y, Huang D, Yu C, and Shi F D. Fingolimod for the treatment of intracerebral hemorrhage: a 2-arm proof-of-concept study. JAMA neurology 71: 1092-1101, 2014.

14. Greiffenstein P, Mathis K W, Stouwe C V, and Molina P E. Alcohol binge before trauma/hemorrhage impairs integrity of host defense mechanisms during recovery. Alcohol Clin Exp Res 31: 704-715, 2007.

15. Hawksworth J S, Graybill J C, Brown T S, Wallace S M, Davis T A, Tadaki D K, and Elster E A. Lymphocyte modulation with FTY720 improves hemorrhagic shock survival in swine. PloS one 7: e34224, 2012.

16. Heckbert S R, Vedder N B, Hoffman W, Winn R K, Hudson L D, Jurkovich G J, Copass M K, Harlan J M, Rice C L, and Maier R V. Outcome after hemorrhagic shock in trauma patients. J Trauma 45: 545-549, 1998.

17. Howard R J, Slesinger P A, Davies D L, Das J, Trudell J R, and Harris R A. Alcohol-binding sites in distinct brain proteins: the quest for atomic level resolution. Alcohol Clin Exp Res 35: 1561-1573, 2011.

18. Jurkovich G J, Rivara F P, Gurney J G, Seguin D, Fligner C L, and Copass M. Effects of alcohol intoxication on the initial assessment of trauma patients. Ann Emerg Med 21: 704-708, 1992.

19. Lee J F, Gordon S, Estrada R, Wang L, Siow D L, Wattenberg B W, Lominadze D, and Lee M J. Balance of S1P1 and S1P2 signaling regulates peripheral microvascular permeability in rat cremaster muscle vasculature. Am J Physiol Heart Circ Physiol 296: H33-42, 2009.

20. Li Q, Chen B, Zeng C, Fan A, Yuan Y, Guo X, Huang X, and Huang Q. Differential activation of receptors and signal pathways upon stimulation by different doses of sphingosine-1-phosphate in endothelial cells. Experimental physiology, 2014.

21. Lu L, Barfejani A H, Qin T, Dong Q, Ayata C, and Waeber C. Fingolimod exerts neuroprotective effects in a mouse model of intracerebral hemorrhage. Brain research 1555: 89-96, 2014.

22. Madan A K, Yu K, and Beech D J. Alcohol and drug use in victims of life-threatening trauma. J Trauma 47: 568-571, 1999.

23. Mathis K W and Molina P E. Transient central cholinergic activation enhances sympathetic nervous system activity but does not improve hemorrhage-induced hypotension in alcohol-intoxicated rodents. Shock 32: 410-415, 2009.

24. Mathis K W, Zambell K, Olubadewo J O, and Molina P E. Altered hemodynamic counter-regulation to hemorrhage by acute moderate alcohol intoxication. Shock 26: 55-61, 2006.

25. Molina M F, Whitaker A, Molina P E, and McDonough K H. Alcohol does not modulate the augmented acetylcholine-induced vasodilatory response in hemorrhaged rodents. Shock 32: 601-607, 2009.

26. Molina P E, Zambell K L, Norenberg K, Eason J, Phelan H, Zhang P, Stouwe C V, Carnal J W, and Porreta C. Consequences of alcohol-induced early dysregulation of responses to trauma/hemorrhage. Alcohol 33: 217-227, 2004.

27. Phelan H, Stahls P, Hunt J, Bagby G J, and Molina P E. Impact of alcohol intoxication on hemodynamic, metabolic, and cytokine responses to hemorrhagic shock. J Trauma 52: 675-682, 2002.

28. Rolland W B, Lekic T, Krafft P R, Hasegawa Y, Altay O, Hartman R, Ostrowski R, Manaenko A, Tang J, and Zhang J H. Fingolimod reduces cerebral lymphocyte infiltration in experimental models of rodent intracerebral hemorrhage. Experimental neurology 241: 45-55, 2013.

29. Samarska I V, Bouma H R, Buikema H, Mungroop H E, Houwertjes M C, Absalom A R, Epema A H, and Henning R H. S1P1 receptor modulation preserves vascular function in mesenteric and coronary arteries after CPB in the rat independent of depletion of lymphocytes. PloS one 9: e97196, 2014.

30. Sammani S, Moreno-Vinasco L, Mirzapoiazova T, Singleton P A, Chiang E T, Evenoski C L, Wang T, Mathew B, Husain A, Moitra J, Sun X, Nunez L, Jacobson J R, Dudek S M, Natarajan V, and Garcia J G. Differential effects of sphingosine 1-phosphate receptors on airway and vascular barrier function in the murine lung. Am J Respir Cell Mol Biol 43: 394-402, 2010.

31. Sanchez T, Estrada-Hernandez T, Paik J H, Wu M T, Venkataraman K, Brinkmann V, Claffey K, and Hla T. Phosphorylation and action of the immunomodulator FTY720 inhibits vascular endothelial cell growth factor-induced vascular permeability. J Biol Chem 278: 47281-47290, 2003.

32. Sanchez T, Skoura A, Wu M T, Casserly B, Harrington E O, and Hla T. Induction of vascular permeability by the sphingosine-1-phosphate receptor-2 (S1P2R) and its downstream effectors ROCK and PTEN. Arterioscler Thromb Vasc Biol 27: 1312-1318, 2007.

33. Shih H C, Hu S C, Yang C C, Ko T J, Wu J K, and Lee C H. Alcohol intoxication increases morbidity in drivers involved in motor vehicle accidents. Am J Emerg Med 21: 91-94, 2003.

34. Tharakan B, Holder-Haynes J G, Hunter F A, Smythe W R, and Childs E W. Cyclosporine A prevents vascular hyperpermeability after hemorrhagic shock by inhibiting apoptotic signaling. J Trauma 66: 1033-1039, 2009.

35. Tharakan B, Hunter F A, Smythe W R, and Childs E W. Alpha-lipoic acid attenuates hemorrhagic shock-induced apoptotic signaling and vascular hyperpermeability. Shock 30: 571-577, 2008.

36. Tharakan B, Hunter F A, Smythe W R, and Childs E W. Curcumin inhibits reactive oxygen species formation and vascular hyperpermeability following haemorrhagic shock. Clin Exp Pharmacol Physiol 37: 939-944, 2010.

37. Tharakan B, Whaley J, Hunter F, Smythe W, and Childs E. (-)-Deprenyl inhibits vascular hyperpermeability after hemorrhagic shock. Shock (Augusta, Ga.) 33: 56-63, 2010.

38. Vonghia L, Leggio L, Ferrulli A, Bertini M, Gasbarrini G, and Addolorato G. Acute alcohol intoxication. Eur J Intern Med 19: 561-567, 2008.

39. Wang L, Chiang E T, Simmons J T, Garcia J G, and Dudek S M. FTY720-induced human pulmonary endothelial barrier enhancement is mediated by c-Abl. The European respiratory journal 38: 78-88, 2011.

40. Wang L, Sammani S, Moreno-Vinasco L, Letsiou E, Wang T, Camp S M, Bittman R, Garcia J G, and Dudek S M. FTY720 (s)-phosphonate preserves sphingosine 1-phosphate receptor 1 expression and exhibits superior barrier protection to FTY720 in acute lung injury. Critical care medicine 42: e189-199, 2014.

41. Whitaker A, Sulzer J, and Molina P. Augmented central nitric oxide production inhibits vasopressin release during hemorrhage in acute alcohol-intoxicated rodents. American journal of physiology Regulatory, integrative and comparative physiology 301: 39, 2011.

We claim:

1. A method for stabilizing blood pressure in a subject having alcohol-induced hypotension, comprising intravenously administering an effective amount of fingolimod, or a pharmaceutically acceptable salt thereof, to the subject, wherein said administering ameliorates the alcohol-induced hypotension.

2. The method of claim 1, wherein the subject is suffering from acute physical trauma at the time of said administering.

3. The method of claim 1, wherein the subject is not suffering from acute physical trauma at the time of said administering.

4. The method of claim 1, wherein the subject is suffering from alcohol-intoxication at the time of said administering, and wherein the method further comprises identifying the subject as being alcohol-intoxicated at the time of said administering.

5. The method of claim 1, wherein the subject is suffering from alcohol-intoxication at the time of said administering, and wherein the method further comprises measuring the extent of alcohol-intoxication in the subject before, during, and/or after said administering.

6. The method of claim 1, wherein the subject is suffering from alcohol-intoxication at the time of said administering, and wherein the method further comprises measuring blood pressure of the subject before, during, and/or after said administering.

* * * * *

UNITED STATES PATENT AND TRADEMARK OFFICE
CERTIFICATE OF CORRECTION

PATENT NO. : 10,111,841 B2
APPLICATION NO. : 15/185802
DATED : October 30, 2018
INVENTOR(S) : Jerome William Breslin and Travis Matthew Doggett Page 1 of 1

It is certified that error appears in the above-identified patent and that said Letters Patent is hereby corrected as shown below:

In the Specification

Column 1,
Lines 16-19, "This invention was made with government support under Grant Number HL098215 awarded by the National Institutes of Health. The government has certain rights in the invention." should read --This invention was made with government support FM120774 and HL098215 awarded by the National Institutes of Health. The Government has certain rights in the invention.--.

Signed and Sealed this
Eighteenth Day of June, 2019

Andrei Iancu
*Director of the United States Patent and Trademark Office*